US011835529B1

(12) United States Patent
Garbett et al.

(10) Patent No.: US 11,835,529 B1
(45) Date of Patent: Dec. 5, 2023

(54) PLASMA THERMOGRAMS FOR DIAGNOSIS AND TREATMENT OF ACUTE MYOCARDIAL INFARCTION

(71) Applicant: The University of Louisville Research Foundation, Inc., Louisville, KY (US)

(72) Inventors: Nichola C. Garbett, Louisville, KY (US); Andrew P. DeFilippis, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 249 days.

(21) Appl. No.: 17/080,533

(22) Filed: Oct. 26, 2020

Related U.S. Application Data

(60) Provisional application No. 62/925,725, filed on Oct. 24, 2019.

(51) Int. Cl.
*G01N 33/53* (2006.01)
*G01N 33/68* (2006.01)

(52) U.S. Cl.
CPC ..... *G01N 33/6887* (2013.01); *G01N 33/6893* (2013.01); *G01N 2333/58* (2013.01); *G01N 2800/324* (2013.01)

(58) Field of Classification Search
None
See application file for complete search history.

(56) References Cited

U.S. PATENT DOCUMENTS

| | | | |
|---|---|---|---|
| 4,952,904 A | 8/1990 | Johnson et al. | |
| 5,225,766 A | 7/1993 | O'Neill | |
| 5,763,433 A | 6/1998 | Morfin | |
| 7,141,210 B2 | 11/2006 | Bell et al. | |
| 7,147,763 B2 | 12/2006 | Elrod et al. | |
| 8,066,429 B2 | 11/2011 | Danley | |
| 8,393,785 B2 | 3/2013 | De Bruyker et al. | |
| 8,685,216 B2 | 4/2014 | De Bruyker et al. | |
| 2007/0242722 A1 | 10/2007 | Nakamura | |
| 2008/0172184 A1 | 7/2008 | Chaires et al. | |
| 2010/0093100 A1 | 4/2010 | Chaires et al. | |
| 2011/0216804 A1 | 9/2011 | Roukes et al. | |
| 2011/0301860 A1 | 12/2011 | Chaires et al. | |
| 2018/0277250 A1 | 9/2018 | Garbett et al. | |
| 2022/0365014 A1 | 11/2022 | Roussel, Jr. et al. | |

FOREIGN PATENT DOCUMENTS

| | | | |
|---|---|---|---|
| EP | 3346262 | 7/2018 | |
| WO | 2008/089072 | 7/2008 | |
| WO | 2010/033606 | 3/2010 | |
| WO | 2011/156658 | 12/2011 | |
| WO | 2012/109383 | 8/2012 | |
| WO | 2017/066800 | 4/2017 | |
| WO | 2017/097854 | 6/2017 | |
| WO | WO2017097854 A1 * | 6/2017 | ............ G01N 33/68 |
| WO | 2021/081524 | 4/2021 | |

OTHER PUBLICATIONS

Braunet al., Stable Coronary Artery Disease: Treatment, American Family Physician, Mar. 15, 2018, vol. 97, No. 6, pp. 376-384. (Year: 2018).*
U.S. Appl. No. 15/764,458, filed Mar. 29, 2018, International filing date Oct. 17, 2016.
U.S. Appl. No. 17/080,805, filed Oct. 26, 2020.
Cooper, A. et al., "Differential scanning microcalorimetry", Protein-Ligand Interactions: hydrodynamics and calorimetry: a practical approach, Oxford University Press, chapter 11, pp. 287-318, (2001).
Johnson, C.M. "Differential scanning calorimetry as a tool for protein folding and stability", Archives of Biochemistry and Biophysics, vol. 531, pp. 100-109, (2013).
Garbett, N.C. et al., "Clinical application of plasma thermograms. Utility, practical approaches and considerations", Methods, vol. 76, pp. 41-50, (2015).
Garbett, N.C. et al., "Differential scanning calorimetry of blood plasma for clinical diagnosis and monitoring", Experimental and Molecular Patholgy, vol. 86, pp. 186-191, (2009).
Garbett, N.C. et al., "Calorimetry outside the box: a new window into the plasma proteome", Biophysical Journal, vol. 94, pp. 1377-1383, (2008).
Garbett, N.C. et al., "Calorimetric analysis of the plasma proteome", Seminars in Nephrology, vol. 27, issue 6, pp. 621-626, (2007).
Garbett, N.C. et al., "Interrogation of the plasma proteome with differential scanning calorimetry", Clinical Chemistry, vol. 53, issue 11, pp. 2012-2014, (2007).
Garbett, N.C., et al., "Ligand binding alters the calorimetric thermogram of albumin", Journal of Clinical Ligand Assay, vol. 29, pp. 194-197, (2006).
Garbett, N.C. et al., "Calorimetric analysis of the plasma proteome: Identification of type 1 diabetes patients with early renal function decline", Biochimica et Biophysica Acta (BBA)—General Subjects, vol. 1830, issue 10, pp. 4675-4680, (2013).
Garbett, N.C. et al., "Detection of cervical cancer biomarker patterns in blood plasma and urine by differential scanning calorimetry and mass spectrometry", PLOS One, vol. 9, issue 1, e84710, (2014).
Chagovetz, A.A. et al., "Preliminary use of differential scanning calorimetry of cerebrospinal fluid for the diagnosis of glioblastoma multiforme", Journal of Neuro-Oncology, vol. 105, pp. 499-506, (2011).
Chagovetz, A.A. et al., "Differential scanning calorimetry of gliomas: a new tool in brain cancer diagnostics?", Neurosurgery, vol. 73, pp. 289-295, (2013).
Fekecs, T. et al., "Differential scanning calorimetry (DSC) analysis of human plasma in melanoma patients with or without regional lymph node metastases", Journal of Thermal Analysis and Calorimetry, vol. 108, pp. 149-152, (2012).

(Continued)

*Primary Examiner* — Gary Counts
(74) *Attorney, Agent, or Firm* — EVAN LAW GROUP LLC

(57) ABSTRACT

A method of diagnosing a patient showing symptoms of acute myocardial infarction includes obtaining a plasma sample from a patient, performing a differential scanning calorimetry test on the sample to produce a thermogram, comparing the thermogram to reference thermograms, and determining if the patient has thrombotic myocardial infarction, non-thrombotic myocardial injury, or stable coronary artery disease.

10 Claims, 9 Drawing Sheets

(56) References Cited

OTHER PUBLICATIONS

Ferencz, A. et al., "Differential scanning calorimetry, as a new method to monitor human plasma in melanoma patients with regional lymph node or distal metastases", Skin Cancer Overview, Dr. Yaguang Xi (Ed.), pp. 141-152, (2011).
Fish, D.J. et al., "Statistical analysis of plasma thermograms measured by differential scanning calorimetry", Biophysical Chemistry, vol. 152, pp. 184-190, (2010).
Krumova, S. et al., "Calorimetric monitoring of the serum proteome in schizophrenia patients", Thermochimica Acta, vol. 572, pp. 59-64, (2013).
Mehdi, M. et al., "Differential scanning calorimetry (DSC) analysis of human plasma in different psoriasis stages", Journal of Thermal Analysis and Calorimetry, vol. 111, pp. 1801-1804, (2013).
Michnik, A. "Blood plasma, serum and serum proteins microcalorimetric studies aimed at diagnosis support", Thermal Analysis in Medical Application, pp. 171-190, (2011).
Michnik, A. et al., "Differential scanning calorimetry study of blood serum in chronic obstructive pulmonary disease", Journal of Thermal Analysis & Calorimetry, vol. 102, pp. 57-60, (2010).
Michnik, A. et al., "DSC serum profiles of sportsmen", Journal of Thermal Analysis & Calorimetry, vol. 113, pp. 365-370, (2013).
Moezzi, M. et al., "Evaluation of blood plasma changes by differential scanning calorimetry in psoriatic patients treated with drugs", Journal of Thermal Analysis & Calorimetry, vol. 116, pp. 557-562, (2014).
Rai, S.N. et al., "Group classification based on high-dimensional data: application to differential scanning calorimetry plasma thermogram analysis of cervical cancer and control samples", Open Access Medical Statistics, vol. 3, pp. 1-9, (2013).
Todinova, S. et al., "Microcalorimetry of blood serum proteome: a modified interaction network in the multiple myeloma case", Analytical Chemistry, vol. 83, pp. 7992-7998, (2011).
Todinova, S. et al., "Calorimetry-based profiling of blood plasma from colorectal cancer patients", Biochimica et Biophysica Acta, vol. 1820, pp. 1879-1885, (2012).
Wisniewski, M.A. et al., "Differential scanning calorimetry in molecular diagnostics", In Vitro Diagnostic Technology, vol. 17, pp. 29-34, (2011).
Zapf, I. et al., "DSC analysis of human plasma in breast cancer patients", Thermochimica Acta, vol. 524, pp. 88-91, (2011).
Vega, S. et al., "Deconvolution analysis for classifying gastric adenocarcinoma patients based on differential scanning calorimetry serum thermograms", Scientific Reports, vol. 5, article No. 7988, pp. 1-8, (2015).
Kikalishvili, L. et al., "Thermal stability of blood plasma proteins of breast cancer patients, DSC study", Journal of Thermal Analysis & Calorimetry, vol. 120, pp. 501-505, (2015).
Zapf, I. et al., "Influence of oxidative injury and monitoring of blood plasma by DSC on breast cancer patients", Journal of Thermal Analysis & Calorimetry, vol. 123, pp. 2029-2035, (2016).
Krumova, S. et al., "Calorimetric features of IgM gammopathies. Implication for patient's diagnosis and monitoring", Thermochimica Acta, vol. 615, pp. 23-29, (2015).
Barceló, F. et al., "Characterization of monoclonal gammopathy of undetermined significance by calorimetric analysis of blood serum proteome", PLOS One, vol. 10, No. 3, e0120316, pp. 1-15, (2015).
Moezzi, M. et al., "Influence of oxidative injury and monitoring of blood plasma by DSC on patients with psoriasis", Journal of Thermal Analysis & Calorimetry, vol. 123, pp. 2037-2043, (2015).
Szalai, Z. et al., "Differential scanning calorimetry (DSC) of blood serum in chronic obstructive pulmonary disease (COPD)", Journal of Thermal Analysis & Calorimetry, vol. 113, pp. 259-264, (2013).
Rasmussen, A. et al., "The lupus family registry and repository", Rheumatology, vol. 50, pp. 47-59, (2011).
Hochberg, M.C., "Updating the american college of rheumatology revised criteria for the classification of systemic lupus erythematosus", Arthritis & Rheumatism, vol. 40, No. 9, p. 1725, (1997).
Ulbricht, J. "Package "lqa" Penalized likelihood inference for GLMs", R package version, pp. 1-42, (2012).
Friedman, J. et al., "Regularization paths for generalized linear models via coordinate descent", Journal of Statistical Software, vol. 33, No. 1, pp. 1-22, (2010).
Becker, N. et al., "penalizedSVM: a R-package for feature selection SVM classification", Bioinformatics, vol. 25, No. 13, pp. 1711-1712, (2009).
Becker, N. et al., "Elastic SCAD as a novel penalization method for SVM classification tasks in high-dimensional data", BMC Bioinformatics, vol. 12, No. 138, pp. 1-13, (2011).
Xu, P. et al., "Modified linear discriminant analysis approaches for classification of high-dimensional microarray data", Computational Statistics & Data Analysis, vol. 53, pp. 1674-1687, (2009).
Witten, D.M. et al., "Penalized classification using Fisher's linear discriminant", Journal of the Royal Statistical Society, Series B, vol. 73, No. 5, pp. 753-772, (2011).
Gaynanova, I. et al., "Simultaneous sparse estimation of canonical vectors in the p >> N setting", Journal of the American Statistical Association, vol. 111, No. 514, pp. 696-706, (2015).
Witten, D. "Package penalizedLDA: Penalized classification using Fisher's linear discriminant", Journal of the Royal Statistical Society, Series B, vol. 73, No. 5, pp. 753-772, (2011).
Gaynanova, I., "MGSDA: Multi-group sparse discriminant analysis", R package version 1.1, pp. 1-8, (2014).
Gromski, P.S. et al., "A tutorial review: Metabolomics and partial least squares-discriminant analysis—a marriage of convenience or a shotgun wedding", Analytica Chimica Acta, vol. 879, pp. 10-23, (2015).
Chun, H. et al., "Sparse partial least squares regression for simultaneous dimension reduction and variable selection", Journal of the Royal Statistical Society, Series B, vol. 72, No. 1, pp. 3-25, (2010).
Chung, D. et al., "Sparse partial least squares classification for high dimensional data", Statistical Applications in Genetics and Molecular Biology, vol. 9, issue 1, article 17, pp. 1-32, (2010).
Kuhn, M., "Building predictive models in R using the caret package", Journal of Statistical Software, vol. 28, issue 5, pp. 1-26, (2008).
Rivero, S.J. et al., "Lymphopenia in systemic lupus erythematosus, clinical, diagnostic, and prognostic significance", Arthritis and Rheumatism, vol. 21, No. 3, pp. 295-305, (1978).
The Autoimmune Diseases Coordinating Committee, "Progress in autoimmune diseases research", National Institutes of Health, U.S. Department of Health and Human Services, (2005).
Illei, G.G. et al., "Biomarkers in systemic lupus erythematosus, II. Markers of disease activity", Arthritis and Rheumatism, vol. 50, No. 7, pp. 2048-2065, (2004).
Ahearn, J.M. et al., "Biomarkers for systemic lupus erythematosus", Translational Research, vol. 159, issue 4, pp. 326-342, (2012).
Liu, C-C. et al., "Cell-bound complement biomarkers for SLE: From benchtop to bedside", Rheumatic Disease Clinics North America, vol. 36, issue 1, pp. 161-172, (2010).
Kalunian, K.C. et al., "Measurement of cell-bound complement activation products enhances diagnostic performance in systemic lupus erythematosus", Arthritis & Rheumatism, vol. 64, No. 12, pp. 4040-4047, (2012).
Benjamini, Y. et al., "Controlling the false discovery rate: a practical and powerful approach to multiple testing", Journal of the Royal Statistical Society, vol. 57, No. 1, pp. 289-300, (1995).
Garbett, N.C. et al., "Differential scanning calorimetry as a complementary diagnostic tool for the evaluation of biological samples", Biochimica et Biophysica Acta (BBA)—General Subjects, vol. 1860, issue 5, pp. 981-989, (2016).
Romero-Diaz, J. et al., "Measures of adult systemic lupus erythematosus: updated version of British Isles Lupus Assessment Group (BILAG 2004), European Consensus Lupus Activity Measurements (ECLAM), Systemic Lupus Activity Measure, Revised (SLAM-R), Systemic Lupus Activity Questionnaire for Population Studies (SLAQ), Systemic Lupus Erythematosus Disease Activity Index 2000 (SLEDAI-2K), and Systemic Lupus International Collaborating Clinics/American College of Rheumatology Damage Index (SDI)", Arthritis Care and Research, vol. 63, issue s11, pp. s37-s46, (2011).

(56) References Cited

OTHER PUBLICATIONS

Petri, M. et al., "Derivation and validation of the Systemic Lupus International Collaborating Clinics classification criteria for systemic lupus erythematosus", Arthritis and rheumatism, vol. 64, No. 8, pp. 2677-2686, (2012).
Anić, F. et al., "New classification criteria for systemic lupus erythematosus correlate with disease activity", Croatian Medical Journal, vol. 55, pp. 514-519, (2014).
International Search Report and Written Opinion dated Jan. 17, 2017 for PCT application No. PCT/US2016/057416, 11 pages, 2017.
"IUPAC-IUB commission on biochemical nomenclature symbols for amino-acid derivatives and peptides recommendations", Biochemistry, vol. 11, No. 9, pp. 1726-1732, (1972).
Heinlen, L.D. et al., "Clinical criteria for systemic lupus erythematosus precede diagnosis, and associated autoantibodies are present before clinical symptoms", Arthritis & Rheumatism, vol. 56, No. 7, pp. 2344-2351, (2007).
International Search Report and Written Opinion dated Apr. 7, 2021 for PCT application No. PCT/US2020/057412, 18 pages, 2018.
Rai, S.N. et al., "Multi-group diagnostic classification of high-dimensional data using differential scanning calorimetry plasma thermograms", Plos One, vol. 14, No. 8, pp. 1-17, (2019).
Melvin, A. et al., "Development of a power-compensated MEMS DSC sensor", (Abstract).
Melvin, A. et al., "Development of a power-compensated MEMS DSC sensor", (Poster).
Tsvetkov, P.O. et al., "An AI-powered blood test to detect cancer using nanoDSF", Cancers, vol. 13, pp. 1-9, (2021).
DeFilippis, A.P. et al., "Assessment and treatment of patients with type 2 myocardial infarction and acute nonischemic myocardial injury", Circulation, vol. 140, pp. 1661-1678, (2019).
DeFilippis, A.P. et al., "Identification of a plasma metabolomic signature of thrombotic myocardial infarction that is distinct from non-thrombotic myocardial infarction and stable coronary artery disease", PLOS One, vol. 12, issue 4, pp. 1-23, (2017).
Go, A.S. et al., "Heart disease and stroke statistics 2014 update: A report from the American heart association", Circulation, vol. 129, No. 3, pp. 1-267, (2014).
Pitts, S.R. et al., "National hospital ambulatory medical care survey: 2006 emergency department summary", National health statistics reports, No. 7, pp. 1-39, (2008).
Newby, L.K. et al., "Accf 2012 expert consensus document on practical clinical considerations in the interpretation of troponin elevations: a report of the American college of cardiology foundation taskforce on clinical expert consensus documents", Journal of the American College of Cardiology, vol. 60, No. 23, pp. 2427-2463, (2012).
Bax, J.J. et al., "Third universal definition of myocardial infarction", Journal of the American College of Cardiology, vol. 60, No. 16, pp. 1581-1598, (2012).
Gore, M.O. et al., "Age-and sex-dependent upper reference limits for the high-sensitivity cardiac troponin t assay", Journal of the American College of Cardiology, vol. 63, No. 14, pp. 1441-1448, (2014).
Javed, U. et al., "Frequency of elevated troponin I and diagnosis of acute myocardial infarction", The American Journal of Cardiology, vol. 104, No. 1, pp. 9-13, (2009).
Wong, P. et al., "Raised cardiac troponin t levels in patients without acute coronary syndrome", Postgraduate Medical Journal, vol. 83, No. 977, pp. 200-205, (2007).
Wang, P. et al., "Effects of comorbidity and hospital care on 6-month mortality inpatients with elevated cardiac troponin t", Postgraduate Medical Journal, vol. 83, No. 979, pp. 332-337, (2007).
Wong, P.S.C. et al., "Early and late mortality in hospitalized patients with raised cardiac troponin t", Postgraduate Medical Journal, vol. 88, No. 1042, pp. 437-442, (2012).
Reeder, G.S. et al., "Overview of the acute management of ST-elevation myocardial infarction", Up to Date, pp. 1-14, found at www.uptodate.com/contents/overview-of-the-acute-management-of-st-elevation-myocardial-infarction?search=Overview of the acute management of ST-elevation myocardial infarction&source=search_result&selectedTitle=1~150&usage_type=default&display_rank=1, (2019).
Reeder, G.S. et al., "Overview of the non-acute management of ST elevation myocardial infarction", Up to Date, pp. 1-12, found at www.uptodate.com/contents/overview-of-the-non-acute-management-of-st-elevation-myocardial-infarction?search=Overview of the non-acute management of ST elevation myocardial infarction&source=search_result&selectedTitle=1~150&usage_type=default&display_rank=1, (2019).
Benjamin, E.J. et al., "Heart Disease and Stroke Statistics—2018 Update: A Report from the American Heart Association", Circulation, vol. 137, pp. e67-e492, (2018).
Thygesen, K. et al., "Fourth Universal Definition of Myocardial Infarction", Circulation, vol. 138, pp. e618-e651, (2018).
Amsterdam, E.A. et al., "2014 AHA/ACC guideline for the management of patients with non-ST-elevation acute coronary syndromes: executive summary: a report of the American College of Cardiology/American Heart Association Task Force on Practice Guidelines", Circulation, vol. 130, pp. 2354-2394, (2014).
Collet, J.P. et al., "2020 ESC Guidelines for the management of acute coronary syndromes in patients presenting without persistent ST-segment elevation", European Heart Journal, vol. 42, pp. 1289-1367, (2021).
Tamis-Holland, J.E. et al., "Contemporary Diagnosis and Management of Patients With Myocardial Infarction in the Absence of Obstructive Coronary Artery Disease: A Scientific Statement From the American Heart Association", Circulation, vol. 139, e891-e908, (2019).
Sarkisian, L. et al., "Prognostic Impact of Myocardial Injury Related to Various Cardiac and Noncardiac Conditions", The American Journal of Medicine, vol. 129, pp. 506-514, (2016).
Pope, J.H. et al., "Missed diagnoses of acute cardiac ischemia in the emergency department", The New England Journal of Medicine, vol. 342, pp. 1163-1170, (2000).
Tatum, J.L. et al., "Comprehensive strategy for the evaluation and triage of the chest pain patient", Annals of Emergency Medicine, vol. 29, pp. 116-125, (1997).
Jneid, H. et al., "2017 AHA/ACC Clinical Performance and Quality Measures for Adults With ST-Elevation and Non-ST-Elevation Myocardial Infarction: A Report of the American College of Cardiology/American Heart Association Task Force on Performance Measures", Journal of the American College of Cardiology, vol. 70, pp. 2048-2090, (2017).
Bueno, H. et al., "Effect of thrombolytic therapy on the risk of cardiac rupture and mortality in older patients with first acute myocardial infarction", European Heart Journal, vol. 26, pp. 1705-1711, (2005).
Wallentin, L. et al., "Efficacy and safety of tenecteplase in combination with the low-molecular-weight heparin enoxaparin or unfractionated heparin in the prehospital setting: the Assessment of the Safety and Efficacy of a New Thrombolytic Regimen (ASSENT)-3 PLUS randomized trial in acute myocardial infarction", Circulation, vol. 108, pp. 135-142, (2003).
Mehta, L.S., "Acute Myocardial Infarction in Women a Scientific Statement from the American Heart Association", Circulation, vol. 133, pp. 916-947, (2016).
Culic, V. et al., "Symptom presentation of acute myocardial infarction: Influence of sex, age, and risk factors", American Heart Journal, vol. 144, No. 6, pp. 1012-1017, (2002).
DeFilippis, A.P. et al., "Myocardial Infarction as a Clinical End Point in Research, What are we really talking about?", Circulation Research, vol. 124, No. 12, pp. 1701-1703, (2019).
Trainor, P.J. et al., "Systems characterization of differential plasma metabolome perturbations following thrombotic and non-thrombotic myocardial infarction", Journal of Proteomics, vol. 160, pp. 38-46, (2017).
Trainor, P.J. et al., "Wisdom of artificial crowds feature selection in untargeted metabolomics: An application to the development of a blood-based diagnostic test for thrombotic myocardial infarction", Journal of Biomedical Informatics, vol. 81, pp. 53-60, (2018).

(56) References Cited

OTHER PUBLICATIONS

Trainor, P.J. et al., "Evaluation of classifier performance for multiclass phenotype discrimination in untargeted metabolomics", Metabolites, vol. 7, No. 30, pp. 1-20, (2017).
Garbett, N.C. et al., "Characterization and classification of lupus patients based on plasma thermograms", PloS One, vol. 12, No. 11, pp. 1-11, (2017).
Kendrick, S.K. et al., "Application and interpretation of functional data analysis techniques to differential scanning calorimetry data from lupus patients", PloS one, vol. 12, No. 11, pp. 1-21, (2017).
Velazquez-Campoy, A. et al., "Thermal liquid biopsy for monitoring melanoma patients under surveillance during treatment: A pilot study", Biochimica et Biophysica acta General subjects, vol. 1862, issue 8, pp. 1701-1710, (2018).
Krumova, S. et al., "Intercriteria analysis of calorimetric data of blood serum proteome", Biochimica et Biophysica acta General subjects, vol. 1861, issue 2, pp. 409-417, (2017).
Todinova, S. et al., "Calorimetric markers for monitoring of multiple myeloma and waldenstrom's macroglobulinemia patients", European Biophysics Journal, vol. 47, pp. 549-559, (2018).
Todinova, S. et al., "Calorimetric markers of Bence Jones and nonsecretory multiple myeloma serum proteome", Analytical Chemistry, vol. 86, pp. 12355-12361, (2014).
Levine, G.N. et al., "2015 ACC/AHA/SCAI Focused Update on Primary Percutaneous Coronary Intervention for Patients With ST-Elevation Myocardial Infarction: An Update of the 2011 ACCF/AHA/SCAI Guideline for Percutaneous Coronary Intervention and the 2013 ACCF/AHA Guideline for the Management of ST-Elevation Myocardial Infarction", Circulation, vol. 133, No. 11, pp. 1135-1147 (2016).
Amsterdam, E. A., et al., "2014 AHA/ACC Guideline for the Management of Patients With Non-ST-Elevation Acute Coronary Syndromes", Circulation, vol. 130, No. 25, pp. e344-e426, (2014).
O'Gara, P.T., et al. "2013 ACCF/AHA Guideline for the Management of ST-Elevation Myocardial Infarction" Circulation, vol. 127, pp. 529-555, (2013).
Kramer, M.C. et al., "Relationship of thrombus healing to underlying plaque morphology in sudden coronary death", Journal of the American College of Cardiology, vol. 55, pp. 122-132, (2010).
Kramer, M.C. et al., "Presence of older thrombus is an independent predictor of long-term mortality in patients with ST-elevation myocardial infarction treated with thrombus aspiration during primary percutaneous coronary intervention", Circulation, vol. 118, pp. 1810-1816, (2008).
Thygesen, K. et al., "Third Universal Definition of Myocardial Infarction", Circulation, vol. 126, pp. 2020-2035, (2012).
Wagner, G.S. et al., "AHA/ACCF/HRS recommendations for the standardization and interpretation of the electrocardiogram: part VI: acute ischemia/infarction: a scientific statement from the American Heart Association Electrocardiography and Arrhythmias Committee, Council on Clinical Cardiology; the American College of Cardiology Foundation; and the Heart Rhythm Society. Endorsed by the International Society for Computerized Electrocardiology", Journal of the American College of Cardiology, vol. 53, pp. 1003-1011, (2009).
Ambrose, J.A. et al., "Angiographic evolution of intracoronary thrombus and dissection following percutaneous transluminal coronary angioplasty (the Thrombolysis and Angioplasty in Unstable Angina [TAUSA] trial)", the American Journal of Cardiology, vol. 79, pp. 559-563, (1997).
Ambrose, J.A. et al., "Adjunctive thrombolytic therapy during angioplasty for ischemic rest angina. Results of the TAUSA trial", Circulation, vol. 90, pp. 69-77, (1994).
Ambrose, J.A. et al., "Angiography in unstable angina", The American Journal of Cardiology, vol. 68, pp. 78B-84B, (1991).
Capone, G. et al., "Frequency of intracoronary filling defects by angiography in angina pectoris at rest", The American Journal of Cardiology, vol. 56, pp. 403-406, (1985).
Dangas, G. et al., "Correlation of angiographic morphology and clinical presentation in unstable angina", Journal of the American College of Cardiology, vol. 29, pp. 519-525, (1997).
Gibson, C.M. et al., "Relationship of the TIMI myocardial perfusion grades, flow grades, frame count, and percutaneous coronary intervention to long-term outcomes after thrombolytic administration in acute myocardial infarction", Circulation, vol. 105, pp. 1909-1913, (2002).
Gibson, C.M. et al., "Relationship of TIMI myocardial perfusion grade to mortality after administration of thrombolytic drugs", Circulation, vol. 101, pp. 125-130, (2000).
Goldstein, J.A. et al., "Multiple complex coronary plaques in patients with acute myocardial infarction", the New England Journal of Medicine, vol. 343, pp. 915-922, (2000).
Zack, P.M. et al., "The occurrence of angiographically detected intracoronary thrombus in patients with unstable angina pectoris", American Heart Journal, vol. 108, pp. 1408-1412, (1984).
Kedra-Krolik, K. et al., "Blood serum calorimetry indicates the chemotherapeutic efficacy in lung cancer treatment", Scientific Reports, vol. 7, issue 1, pp. 1-5, (2017).
Liaw, A. et al., "Classification and regression by randomForest", R News, vol. 2/3, pp. 18-22, (2002).
Qi, Y., "Random forest for bioinformatics", Ensemble Machine Learning Methods and Applications, chapter 11, pp. 307-323, (2012).
Denoyer, L. et al., "Deep sequential neural network", EWRL 2015—Workshop Deep Learning NIPS, pp. 1-9, (2014).
Ketkar, N., "Introduction to keras", Deep Learning with Python, pp. 95-109, (2017).
Fernandez-Delgado, M. et al., "Do we need hundreds of classifiers to solve real world classification problems?", Journal of Machine Learning Research, vol. 15, pp. 3133-3181, (2014).
Wang, L. et al., "Demonstration of MEMS-based differential scanning calorimetry for determining thermodynamic properties of biomolecules", Sensors and Actuators B: Chemical, vol. 134, pp. 953-958, (2008).
Yu, S. et al., "Review of MEMS differential scanning calorimetry for biomolecular study", Frontiers of Mechanical Engineering, vol. 12, No. 4, pp. 526-538, (2017).
Jia, Y. et al., "A polymer-based MEMS differential scanning calorimeter", Sensors and Actuators A: Physical, vol. 231, pp. 1-7, (2015).
Wang, B. et al., "MEMS-based AC differential scanning calorimetry", 2011 16th International Solid-State Sensors, Actuators and Microsystems Conference, pp. 1958-1961, (2011).
Wang, B. et al., "A MEMS differential scanning calorimeter for thermodynamic characterization of biomolecules", 2011 IEEE 24th International Conference on Micro Electro Mechanical Systems, pp. 821-824, (2011).
Wang, B. et al., "A MEMS differential-scanning-calorimetric sensor for thermodynamic characterization of biomolecules", Journal of Microelectromechanical Systems, vol. 21, No. 5, pp. 1165-1171, (2012).
Wang, L. et al., "A MEMS thermal biosensor for metabolic monitoring applications", Journal of Microelectromechanical Systems, vol. 17, No. 2, pp. 318-327, (2008).
Todinova, S. et al., "Blood plasma thermograms dataset analysis by means of intercriteria and correlation analyses for the case of colorectal cancer", International Journal Bioautomation, vol. 20, No. 1, pp. 115-124, (2016).
Michnik, A. et al., "Differences in cryostimulation and sauna effects on post-exercise changes in blood serum of athletes", Complementary Therapies in Medicine, vol. 51, pp. 1-6, (2020).
Lorinczy, D., et al., "Comparison of deconvoluted plasma DSC curves on patients with solid tumors", Journal of Thermal Analysis and Calorimetry, vol. 142, pp. 1243-1248, (2020).
Jaggi, R.D. et al., "Microfluidic depletion of red blood cells from whole blood in high-aspect-ratio microchannels", Microfluid, Nanofluidics, vol. 3, No. 1, pp. 47-53, (2007).
Rodriguez-Villarreal, A.I. et al., "High flow rate microfluidic device from blood plasma separation using a range of temperatures", Lab Chip, vol. 10, No. 2, pp. 211-219, (2010).

(56) References Cited

OTHER PUBLICATIONS

Kersaudy-Kerhoas, M. et al., "Validation of a blood plasma separation system by biomarker detection", Lab Chip, vol. 10, No. 12, pp. 1587-1595, (2010).
Tripathi, S. et al., "Blood plasma separation in elevated dimension t-shaped microchannel", Biomedical Microdevices, vol. 15, No. 3, pp. 415-425, (2013).
Lee, M.G. et al., "Inertial blood plasma separation in a contraction-expansion array microchannel", Applied Physics Letters, vol. 98, No. 25, pp. 253702-1-253702-3, (2011).
Blattert, C. et al., "Separation of blood in microchannel bends", The 26$^{th}$ Annual International Conference of the IEEE Engineering in Medicine and Biology Society, vol. 1, pp. 2627-2630, (2004).
Tripathi, S. et al., "Microdevice for plasma separation from whole human blood using bio-physical and geometrical effects", Science Reports, vol. 6, pp. 1-15, (2016).
Prabhakar, A. et al., "A novel, compact and efficient microchannel arrangement with multiple hydrodynamic effects for blood plasma separation", Microfluidics and Nanofluidics, vol. 18, No. 5-6, pp. 995-1006, (2015).
Kersaudy-Kerhoas, M. et al., "Micro-scale blood plasma separation: from acoustophoresis to egg-beaters", Lab on a Chip, vol. 13, No. 17, pp. 3323-3346, (2013).
Tripathi, S. et al., "Passive blood plasma separation at the microscale: a review of design principles and microdevices", Journal of Micromechanics and Microengineering, vol. 25, No. 8, pp. 1-24, (2015).
Yu, Z.T.F. et al., "Microfluidic blood cell preparation: now and beyond", Small, vol. 10, No. 9, pp. 1687-1703, (2014).
Wu, D. et al., "How long can we store blood samples: a systematic review and meta-analysis", EBioMedicine, vol. 24, pp. 277-285, (2017).
Dean, L., "Blood groups and red cell antigens", National Center for Biotechnology Information, pp. 1-86, (2005).
Laser, D. J. et at., "A review of micropumps", Journal of Micromechanics and Microengineering, vol. 14, pp. R35-R64 (2004).
Au, A.K. et al., "Mail-order microfluidics: evaluation of stereolithography for the production of microfluidic devices", Lab on a Chip, vol. 7, pp. 1294-1301, (2014).
Au, A.K. et al., "3D-printed microfluidic automation", Lab on a Chip, vol. 15, No. 8, pp. 1934-1941, (2015).
Lee, Y.S. et al., "3D-printed Quake-style microvalves and micropumps", Lab on a Chip, vol. 18, No. 8, pp. 1207-1214 (2018).
Melvin, A.M. et al., "Modeling 3D printed check valves for microfluidic systems", 2018 IEEE International Symposium on Signal Processing and Information Technology (ISSPIT), pp. 179-184, (2018).
Buscaglia, R. et al., "Segment-wise nonparametric classification of multivariate functional data: lupus identification using plasma thermograms", Journal of Applied Statistics, pp. 1-47, (2018).
Aguilera, A.M. et al., "Functional analysis of chemometric data", Open Journal of Statistics, vol. 3, pp. 334-343, (2013).
Wallig, M. et al., "Foreach parallel adaptor for the parallel package", Microsoft Corporation R package version 1, pp. 1-4, (2020).
Berrendero, J.R. et al., "Variable selection in functional data classification: a maxima-hunting proposal", Statistica Sinica, vol. 26, pp. 619-638, (2016).
Caruana, R. et al., "Ensemble selection from libraries of models", Proceedings of the twentyfirst international conference on Machine learning, ACM, pp. 1-8, (2004).
Delaigle, A. et al., "Componentwise classification and clustering of functional data", Biorfietrika, vol. 99, pp. 299-313, (2012).
Dietterich, T.G. et al., "Ensemble methods in machine learning", International Workshop on Multiple Classifier Systems, pp. 1-15, (2000).
Dietterich, T.G., "Ensemble learning", The handbook of brain theory and neural networks, pp. 405-408, (2002).
Dudani, S.A., "The distance-weighted k-nearest-neighbor rule", IEEE Transactions on Systems, Man and Cybernetics, pp. 325-327, (1976).
Febrero-Bande, M. et al, "Statistical computing in functional data analysis: The R package fda.usa", Journal of Statistical Software, vol. 51, pp. 1-28, (2012).
Ferraty, F. et al., "Curves discrimination: a nonparametric functional approach", Computational Statistics & Data Analysis, vol. 44, pp. 161-173, (2003).
Gul, A. et al., "Ensemble of a subset of kNN classifiers", Advances in Data Analysis and Classification, vol. 12, pp. 827-840, (2016).
Hastie, T. et al., "Penalized discriminant analysis", The Annals of Statistics, vol. 23, pp. 73-102, (1995).
Hechenbichler, K. et al., "Weighted k-nearest-neighbor techniques and ordinal classification", Sonderforschungsbereich, vol. 386, paper 399, pp. 1-16, (2004).
Kohavi, R. et al., "Wrappers for feature subset selection", Artificial Intelligence, vol. 97, pp. 273-324, (1997).
Krier, C. et al., "Supervised variable clustering for classification of NIR spectra", Proceedings of the 17$^{th}$ European Symposium on Artificial Neural Networks—Advances in Computatuional Intelligence and Learning (ESANN 2009), pp. 263-268, (2009).
Li, B. et al., "Classification of functional data: A segmentation approach", Computational Statistics & Data Analysis, vol. 52, pp. 4790-4800, (2008).
Muller, K.R. et al., "An introduction to kernel-based learning algorithms", IEEE Transactions on Neural Networks, vol. 12, No. 2, pp. 181-201, (2001).
Parzen, E. "On estimation of a probability density function and mode", The Annals of Mathematical Statistics, vol. 33, issue 3, pp. 1065-1076, (1962).
Porro-Munoz, D. et al., "Dissimilarity representation on functional spectral data for classification", Journal of Chemometrics, vol. 25, No. 9-10, pp. 476-486, (2011).
Ristoski, P. et al., "Feature selection in hierarchical feature spaces", International Conference on Discovery Science, 17$^{th}$ International Conference, pp. 288-300, (2014).
Rizwan, M. et al., Comparison of Distance Metrics for Phoneme Classification based on Deep Neural Network Features and Weighted k-NN Classifier, Georgia Institute of Technology, pp. 1-5, (2014).
Rokach, L., "Ensemble-based classifiers", Artificial Intelligence Review, vol. 33, pp. 1-39, (2010).
Tibshirani, R. et al., "Sparsity and smoothness via the fused lasso", Journal of the Royal Statistical Society: Series B (Statistical Methodology), vol. 67, part 1, pp. 91-108, (2005).
Yang, P. et al., "A review of ensemble methods in bioinformatics", Current Bioinformatics, vol. 5, pp. 296-308, (2010).
Cambon, A.C. et al., "Classification of clinical outcomes using high-throughput informatics: Part 1—nonparametric method reviews", Model Assisted Statistics and Applications, vol. 10, pp. 3-23, (2015).
Cambon, A.C. et al., "Classification of clinical outcomes using high-throughput informatics: Part 2—parametric method reviews", Model Assisted Statistics and Applications, vol. 10, pp. 89-107, (2015).
Melvin, A. et al., "Design and simulation of 3D printed check valves using fluid-structure interaction", 1 page, Aug. 2018, (Poster).
Melvin, A. et al., "A 3D printed microfluidic manifold to separate plasma from whole blood", GSC Presentation, 1 page, Poster, Feb. 28, 2019.
Melvin, A. et al., "A 3D printed microfluidic manifold to separate plasma from whole blood", GSC Presentation, pp. 1-15, Feb. 28, 2019.
Braun, M.M. et al., "Stable coronary artery disease: Treatment", American Family Physician, vol. 97, No. 6, pp. 376-384, (2018).
Jun. 27, 2023, U.S. Appl. No. 15/764,458.
Jul. 24, 2023, U.S. Appl. No. 17/080,533.

* cited by examiner

PLASMA THERMOGRAMS FOR DIAGNOSIS AND TREATMENT OF ACUTE MYOCARDIAL INFARCTION

BACKGROUND

Cardiovascular disease (CVD) is the leading cause of death in the United States and the World. A myocardial infarction (heart attack) is the quintessential cause of CVD in both men and women (1). Despite the frequency of myocardial infarction, diagnosis remains a challenge for individual patients and the health care system (2). Historically defined symptoms for heart attacks include chest pain, difficulty breathing, or fatigue during exertion or at rest. However, one-third of all patients with a myocardial infarction may experience atypical symptoms or no symptoms at all (2, 3) and findings on an electrocardiogram (ECG) are now well recognized to lack sensitivity and/or specificity for myocardial infarction (3). The current non-invasive diagnostic gold standard for myocardial infarction is circulating troponin, with estimates exceeding 50 million tests performed annually in the United States alone. While the cardiac troponin test is very sensitive and specific for detecting myocardial injury, myocardial injury is a broad diagnostic category caused by several distinct mechanisms that result in several categories of myocardial injury (several distinct diagnoses) defined by international consensus (2, 3). Myocardial infarction is a specific type of myocardial injury that requires specific treatment (2,4). Furthermore, within the category of myocardial infarction, several subtypes of myocardial infarction are recognized and necessitate different treatment. Imaging diagnostics including computerized topography (CT) and invasive angiograms can aid in the diagnosis of myocardial infarction but require specialized equipment, subspecialty trained physicians and are expensive, and are thus not readily available at most medical facilities on an emergent basis (2). Furthermore, these diagnostics are limited in their diagnostic sensitivity and specificity for the specific types of myocardial injury and myocardial infarction subtypes (2).

The quintessential myocardial infarction is a myocardial infarction secondary to coronary plaque disruption leading to a thrombotic obstruction of coronary blood flow and resulting myocardial ischemia and necrosis—this myocardial infarction is known as a thrombotic or type 1 myocardial infarction as defined by an international consensus document from the European Society of Cardiology, the American College of Cardiology, the American Heart Association, and the World Health Federation (4). All therapeutics recommended by current consensus guidelines for the treatment of acute myocardial infarction are limited to thrombotic (type 1) MI only (2-7). While recommendations exist for the treatment of non-thrombotic (e.g., type 2) myocardial injury, randomized clinical trials to validate the efficacy of such treatments are limited due to the absence of a clinically actionable diagnostic test to diagnose and differentiate such myocardial injuries from acute thrombotic (type 1) myocardial infarction (2, 8). Therefore, physicians' ability to optimally treat patients with myocardial injury and/or myocardial infarction is limited by the lack of a non-invasive tool to allow for the early identification and differentiation of the different types of myocardial injury and/or myocardial infarction that require timely and different treatment. For example, in a patient suspected of a heart attack, an elevated troponin level confirms the presence of dead heart muscle (myocardial injury), but does not diagnose the cause of the dead heart muscle (myocardial injury). In the absence of direct assessment of the event of interest, the precipitant (and therapeutic target) of acute MI, the treatment of acute MI is often misdirected (FIG. 1).

The non-specificity of troponin for differentiation of myocardial injury types or myocardial infarction subtypes has been demonstrated. One study found that 42% of all troponin tests ordered in a large hospital system were positive, of which only 31% were due to thrombotic MI—the remaining could be attributed to non-thrombotic myocardial injuries (9). Similar results have been reported in other studies (10-14). The limitations of current diagnostic strategies are highlighted by the fact that 70% of the ~6 million US patients presenting to hospital with chest pain concerning for MI are given a benign diagnosis at the cost of approximately $10 billion per year (15-17). Despite the expense of this diagnostic work up, 2-5% of patients discharged with a benign diagnosis are subsequently found to have an acute MI with a worse prognosis than those correctly diagnosed on the initial encounter (15-17). Given the clear difference in the pathobiology resulting in the different types of myocardial injury and subtypes of myocardial infarction, but lack of clinically actionable diagnostics to identify and differentiate these different causes of myocardial injury, the current state of the art care is largely based on circumstantial evidence for the initial management of many patients with myocardial injury (2, 3). This issue is compounded by the need for timely treatment of patients with thrombotic (type 1) MI with anti-thrombotic, anti-coagulant, fibrinolytic and procedural revascularization therapies—delay in such treatment results in greater myocardial injury and worsening patient outcomes, including death. Time to treatment for patients with thrombotic (type 1) MI is so important that it is a major quality metric measured by professional societies and payers like the Centers for Medicare & Medicaid Services (7, 18). However, these same lifesaving, time-sensitive, anti-thrombotic, anti-coagulant, fibrinolytic and procedural revascularization therapies impart a significant risk of bleeding and procedural complications. For example, fibrinolytic therapy for suspected thrombotic (type 1) MI carries a risk of intracerebral hemorrhage of 0.17-6.7% (19-21). Therefore, while timely anti-thrombotic, anti-coagulant, fibrinolytic and procedural revascularization therapies are life saving for patients with thrombotic (type 1) MI, these same therapies are expected to impart significant bleeding and procedural risk, with no significant benefit, for patients with non-thrombotic causes of myocardial injury (defined by cardiac troponin testing). Women are disproportionally affected secondary to the higher frequency of historically "non-classic", non-thrombotic (non-type 1) MI (2, 22) and lack of historically "classic" MI symptoms (23). Clearly, additional approaches are needed for early, point-of-care diagnosis and/or differentiation of thrombotic and acute non-thrombotic myocardial injury events to allow for more efficient, efficacious and timely treatment of the millions of patients presenting with symptoms concerning for acute MI (24).

Differential scanning calorimetry (DSC) profiles (or thermograms) indicate the heat change (excess specific heat capacity) in a fluid sample as it is heated and provides a profile of a sample with minimal processing in approximately two hours. DSC thermograms represent complex mixtures of heat release (exothermic reaction) and heat absorption (endothermic reaction) reflective of the overall biomolecular makeup of the sample (for example, biomolecule concentration, structure, modifications, interactions) at the time of collection. Therefore, DSC is distinct from the majority of clinically available biomarkers, which are measures of a single analyte, typically a single characteristic of the analyte (for example, concentration), as opposed to the complex biological milieu resulting in a pathological state. Atherothrombosis results from an imbalance between dozens of known, and likely hundreds of unknown, thrombotic and fibrinolytic proteins and metabolites that cannot be reflected via individual measurement of the components.

In a small MI patient cohort (n=38 patients), we measured the relative concentration of 1032 circulating metabolites at the time of presentation (acute phase) and 6 months later (follow-up phase) (25). The changes in individual metabolites or classes of metabolites at the time of thrombotic MI versus follow-up state were compared with changes in non-thrombotic myocardial injury (myocardial necrosis control) and stable coronary artery disease subjects (atherosclerosis control) over the same time course via multiple statistical approaches, including our machine learning algorithm (25-28). These analyses identified 5 classes of metabolites which are significantly and specifically associated with thrombotic MI (distinct from non-thrombotic myocardial injury): amino acids, lysophospholipids, monoacylglycerols, steroid hormones, and butyrates (FIG. 2). Importantly, one of our proof of concept algorithms demonstrated the ability to detect and differentiate thrombotic MI from non-thrombotic myocardial injury using metabolites with 93% accuracy, 100% sensitivity, and 90% specificity (25). And, one of our machine learning algorithms had an estimated performance of correctly classifying the type of myocardial injury 97.4% of the time (27).

SUMMARY

In a first aspect, the invention is a method of diagnosing a patient showing symptoms of acute myocardial infarction that includes obtaining a plasma sample from a patient, performing a differential scanning calorimetry test on the sample to produce a thermogram, comparing the thermogram to reference thermograms, and determining if the patient has thrombotic myocardial infarction, non-thrombotic myocardial injury, or stable coronary artery disease.

In a second aspect, the invention is a method of diagnosing and treating a patient showing signs and/or symptoms of acute myocardial infarction that includes obtaining a plasma sample from a patient; performing a differential scanning calorimetry test on the sample to produce a thermogram; comparing the thermogram to reference thermograms; determining if the patient has thrombotic myocardial infarction, non-thrombotic myocardial injury, or stable coronary artery disease; and administering a treatment to the patient based on the thermogram specific to the type of myocardial injury identified by the thermogram.

In a third aspect, the invention is a method that includes obtaining a plasma sample from a patient showing signs and/or symptoms of acute myocardial infarction, and performing a differential scanning calorimetry test on the sample to produce a thermogram.

In a fourth aspect, the invention is a method of preparing reference thermograms that includes identifying patients with a thrombotic myocardial infarction, non-thrombotic myocardial injury and stable coronary artery disease (CAD), obtaining a plurality of plasma samples of the patients, and performing a differential scanning calorimetry test on the samples to produce a plurality of thermograms.

Definitions

"Distinguishing features" refers to the features of a thermogram profile that are different for different patient groups. Distinguishing features may also be referred to as thermogram metrics. For example, the thermograms of patients having coronary atherothrombosis (type 1 MI) acute myocardial injury may be distinguished from the thermograms of patients having infarction caused by pathology other than coronary atherothrombosis (type 2 MI and acute non-ischemic myocardial injury), or stable coronary artery disease (CAD) by comparing the distinguishing features of the thermograms.

BRIEF DESCRIPTION OF THE DRAWINGS

The invention can be better understood with reference to the following drawings and description.

DETAILED DESCRIPTION

Figure 1:
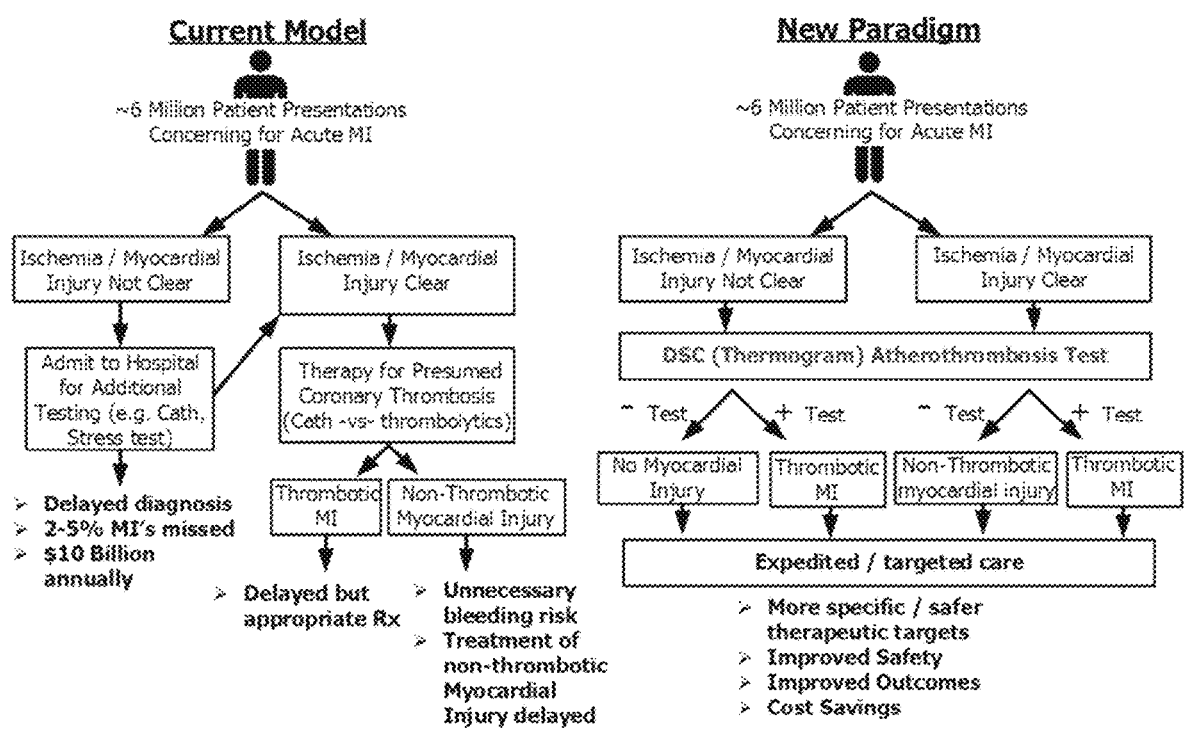
FIG. 1 illustrates current and proposed paradigms for the treatment of patients presenting with signs or symptoms concerning for acute MI.
Figure 2:
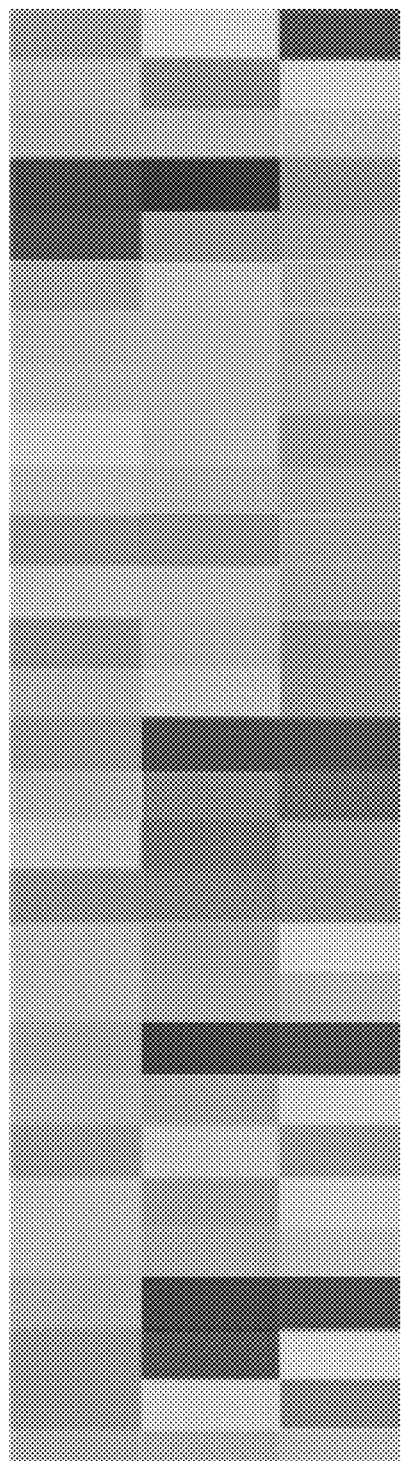
FIG. 2 illustrates a heat map of average relative baseline abundance —metabolites demonstrating consistent discriminatory performance in sparce (few metabolite) classifiers.

Development of a non-invasive, readily available, and safe test to identify and differentiate the types of myocardial injury, including acute myocardial infarction subtypes, will allow for earlier, etiologically informed treatment of specific MI subtypes, resulting in the minimization of ischemic injury and limiting pharmacological and procedural interventions (and associated side effects) to only those likely to benefit. Simply stated, physicians will have more than circumstantial evidence to make timely decisions on the use of anti-thrombotic, anti-coagulant, fibrinolytic and procedural revascularization therapies for patients suspected of a heart attack and/or evidence of myocardial injury (a positive troponin test).

DSC thermograms are distinct at acute presentation among myocardial infarctions caused by coronary atherothrombosis (type 1 MI) acute myocardial injury, infarction caused by pathology other than coronary atherothrombosis (type 2 MI and acute non-ischemic myocardial injury), and stable coronary artery disease (CAD; non-acute atherosclerosis control). Thermograms are consistent with a healthy profile for all three clinical groups at a quiescent phase (three-months after diagnostic evaluation for acute myocardial injury or stable coronary artery disease with coronary angiography). These data suggest that DSC is sensitive to changes in circulating disease-related biomarkers of MI that can diagnose and differentiate between clinically relevant subtypes of myocardial injury, including subtypes of MI.

The present invention includes a unique human cohort using novel research criteria to distinguish thrombotic MI, acute non-thrombotic myocardial injury, and stable CAD. Since thrombosis is a dynamic process, we leveraged the ability of thermograms to report changes between the time of acute disease presentation (that is, active atherothrombosis) and a quiescent phase follow-up (3 months later) (N=40 patients). We also demonstrated the ability of DSC to detect and differentiate thrombotic MI from acute non-thrombotic myocardial injury and stable CAD using only the presenting time-point thermogram profiles. Specific thermogram metrics (for example, localized thermogram features, principal components, deconvolution components) at the time of acute thrombotic MI (FIG. 4 & FIG. 6) are specific to and therefore can be used to differentiate between thrombotic MI, non-thrombotic myocardial injury and stable CAD.

A physician may use a thermogram from a patient to determine the likelihood that a patient has a certain condition by comparing the patient's thermogram to reference thermograms. The patient thermograms will typically not match any reference thermogram exactly, but by identifying the number and similarity of distinguishing features, the physician may determine that it is more or less likely that the patient has thrombotic myocardial injury, non-thrombotic myocardial injury or stable CAD. The thermogram would allow the physician to make informed treatment decisions that would not be possible otherwise.

Figure 3:
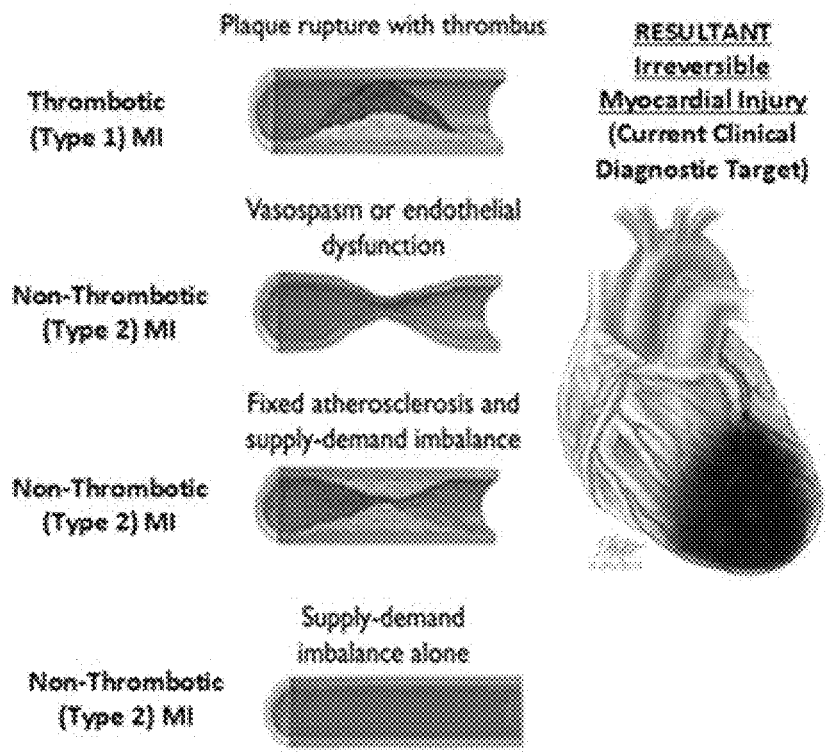
FIG. 3 illustrates etiologically distinct causes and international consensus of diagnostic subtypes of myocardial infarction versus target of current clinically available state of the art diagnostics.

The principal distinction between thrombotic and acute non-thrombotic myocardial injury is the presence of a thrombus. However, prompt identification of thrombus before deciding therapy is difficult; hence biomarkers of thrombus formation are needed to guide clinical care (FIGS. 1 and 3). The novel application of DSC in our laboratory for characterizing human disease has yielded significant preliminary data to suggest that differences in the thermodynamic properties of human plasma proteins can be used to differentiate clinical samples based on health status (28-37). We and others have demonstrated dramatic differences in thermogram profiles in multiple specific diseases, including multiple cancers (cervical, ovarian, endometrial, colorectal, gastric, lung, multiple myeloma, breast, melanoma, brain), autoimmune (systemic lupus erythematosus, rheumatoid arthritis) and other diseases (Lyme disease, diabetes, chronic obstructive pulmonary disease) (29-49).

A whole blood sample may be obtained from a standard venous blood draw, a peripheral intravenous catheter, or a central line catheter. In order to prepare the sample for DSC, plasma will be prepared from the whole blood and diluted to provide an appropriate total volume and to dilute the protein concentration in the plasma to provide a reliable DSC signal. The sample may also be prepared by filtering the plasma sample.

The standard method for the preparation of patient plasma specimens for DSC analysis is as follows: (1) buffer exchange to a physiological reference buffer (for example, buffered-saline) for DSC analysis; (2) buffer and sample filtration; and (3) dilution to a total protein concentration to provide a suitable DSC signal. Step (1) ensures that the solvent composition of the patient sample exactly matches the DSC reference buffer such that the excess heat absorbed by the sample can be attributed to the heat capacity of the constituents of the sample. This step also serves to normalize the buffer for different patient specimen types, for example vacutainers with no anticoagulant (serum); and different anticoagulant types (plasma specimens). Step (2) removes particulates from samples and buffers. Thermal convection of particulates suspended in solution could cause noise in the DSC signal. Step (3) provides a suitable analysis concentration, high enough to provide a suitable DSC signal-to-noise and low enough to avoid excessive plasma protein aggregation and precipitation that occurs following the unfolding transition of interest.

Figure 4:
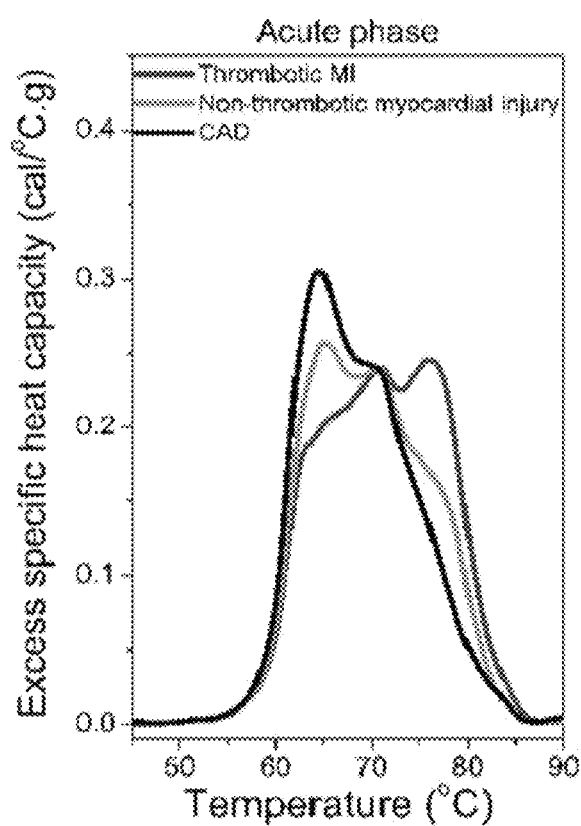
FIG. 4 illustrates the mean thermograms of serum samples collected at acute presentation from thrombotic MI (N=17; red line), acute non-thrombotic myocardial injury (N=9; green line) and stable CAD (N=14; black line) patients.
Figure 5:
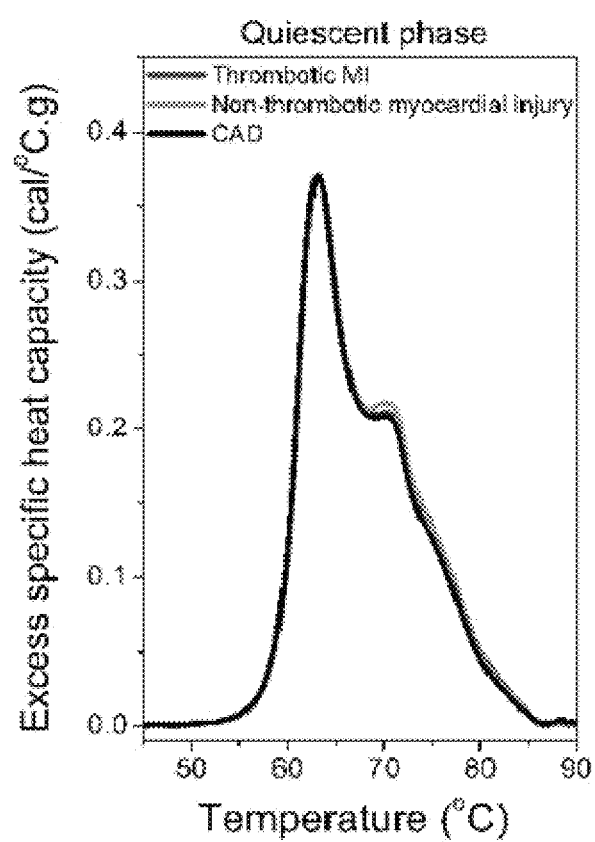
FIG. 5 illustrates thermograms from the same subjects as shown in FIG. 4 at a quiescent phase follow-up (3 months later).

We have applied DSC thermograms to characterize myocardial injury and found that thermograms are distinct among thrombotic MI, acute non-thrombotic myocardial injury (including non-thrombotic MI) and stable coronary artery disease (CAD) at the time of acute presentation (FIGS. 4 and 5). Furthermore, we have shown that the thermograms in the same subjects are indistinguishable with resolution of the acute insult-a quiescent phase follow-up three months later (FIGS. 4 and 5). Our results show that thermograms are able to identify and distinguish thrombotic MI from acute non-thrombotic myocardial injury and stable CAD at the time of acute disease presentation.

Figure 6:
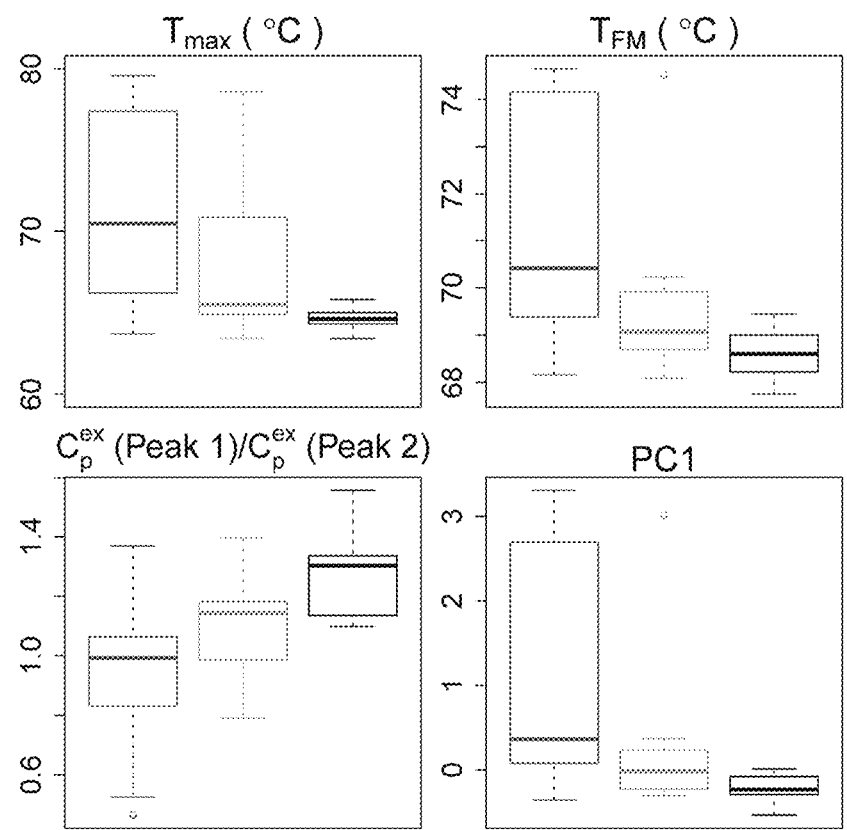
FIG. 6 illustrates boxplots of DSC thermogram metrics at $T_0$ (time of enrollment; acute phase), which show notable differences between acute thrombotic MI (red) from acute non-thrombotic myocardial injury (green) and stable CAD (black).
Figure 7:
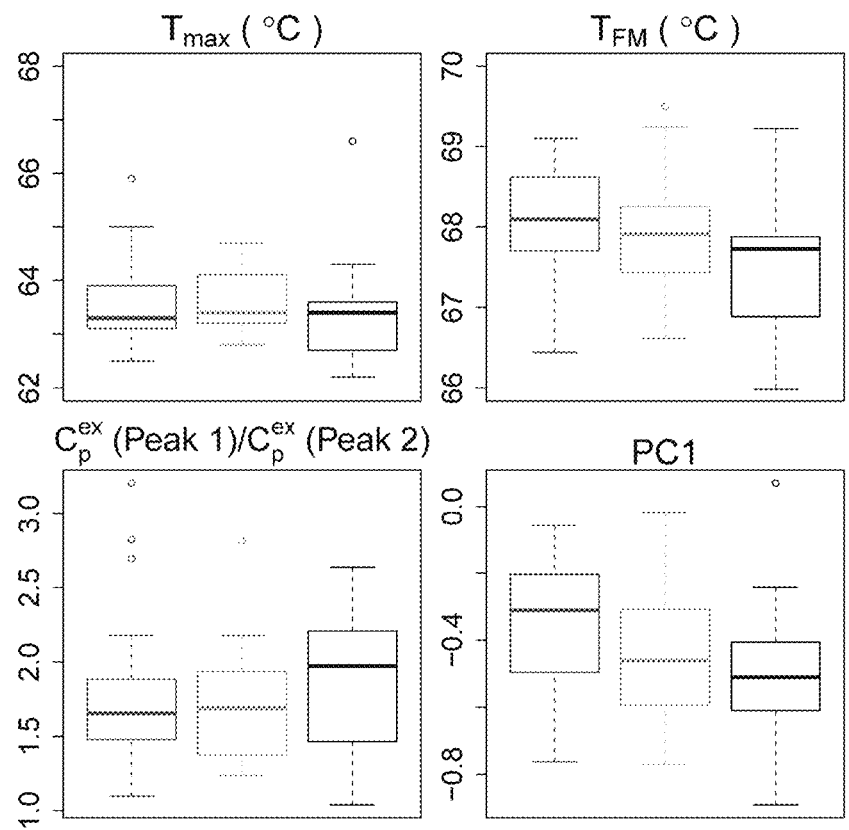
FIG. 7 illustrates DSC thermogram metrics at $T_{FU}$ (3-month follow-up; quiescent phase), which show similar values in the acute thrombotic MI (red), acute non-thrombotic myocardial injury (green) and stable CAD (black) subjects.

Interpretation of changes in thermogram profiles between patient groups is facilitated through the calculation of multiple thermogram shape and feature metrics including: (1) thermogram peak width at half height (width); (2) maximum profile height (height); (3) temperature of the profile maximum ($T_{max}$); (4) first moment temperature ($T_{FM}$) representing the weighted center of the profile; (5) excess specific heat capacity ($C_p^{ex}$) of the first thermogram peak in the range 62-67° C. ($C_p^{ex}$ Peak 1); (6) excess specific heat capacity of the second thermogram peak in the range 69-73° C. ($C_p^{ex}$ Peak 2); (7) ratio of $C_p^{ex}$ Peak 1 to $C_p^{ex}$ Peak 2; and (8) principal components. Statistically significant differences between thrombotic MI, acute non-thrombotic myocardial injury, and stable CAD at time $T_0$ were observed for $T_{max}$, $C_p^{ex}$ Peak 1 to $C_p^{ex}$ Peak 2 ratio, $T_{FM}$ and PC1 (all false-discovery rate (FDR) adjusted p-values <0.05; FIG. 6). In contrast, none of the summary metrics were significantly different between the three groups at $T_{FU}$ (all FDR adjusted p-values >0.9; FIG. 6). $T_{max}$, $C_p^{ex}$ Peak 1 to $C_p^{ex}$ Peak 2 ratio, $T_{FM}$ and PC1 also had a significant mean intra-subject change between the acute (To) and quiescent three-month follow-up ($T_{FU}$) time point for thrombotic MI subjects, with $T_{max}$, and $T_{FM}$ having significantly more pronounced changes in those subjects compared to acute non-thrombotic myocardial injury and stable CAD subjects (FIGS. 6 and 7).

Figure 8:
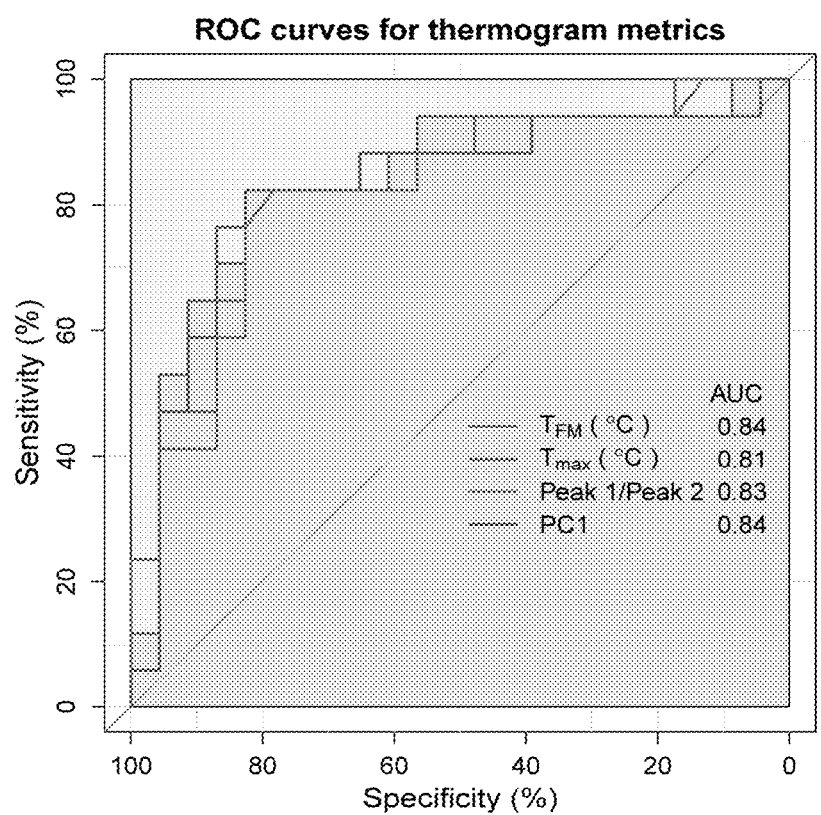
FIG. 8 illustrates ROC curves for four different DSC thermogram metrics at $T_0$.

The data showed that several of the metrics based on thermograms ($T_{FM}$, $T_{max}$, Peak 1/Peak 2 ratio and PC1) were able to distinguish between thrombotic MI and reference groups (acute non-thrombotic myocardial injury and stable CAD) with fairly high accuracy (area under the curve (AUC) values all >0.8, FIG. 8). An area of 1 represents a perfect test, with regard to sensitivity and specificity; an area of 0.5 represents that the test has no discriminatory ability.

Figure 9:
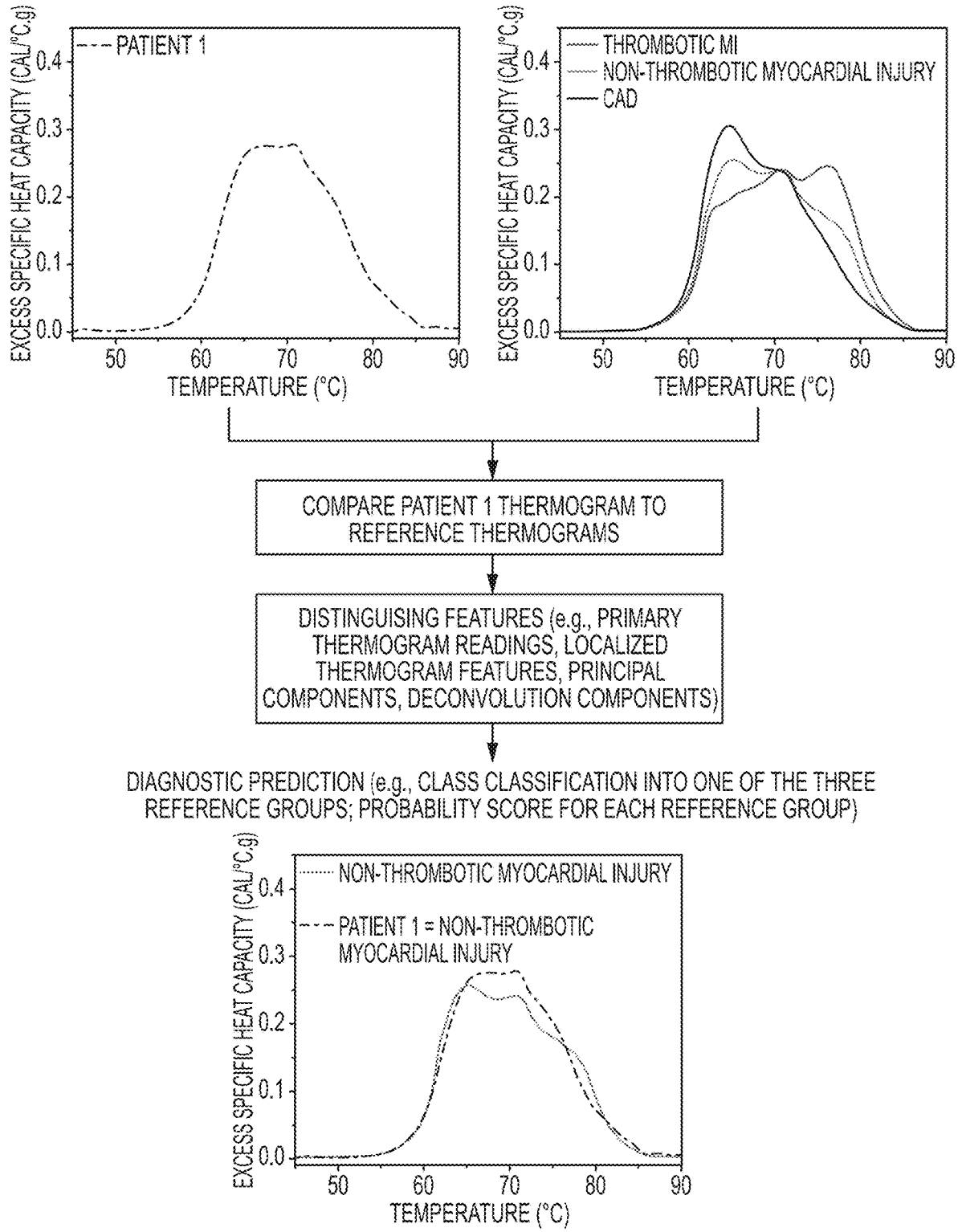
FIG. 9 illustrates a flowchart of the process for diagnosing a patient presenting to medical attention for signs and/or symptoms concerning for a heart attack. The patient's thermogram is rapidly and non-invasively produced and compared to reference thermograms for acute thrombotic MI, non-thrombotic myocardial injury and stable CAD. A diagnostic classifier provides the probability of the patient's thermogram matching each of the three diagnostic reference groups to aid in the medical management of the patient (FIG. 1).

FIG. 9 illustrates a flow chart showing the use of DSC thermograms for diagnosing and/or differentiating between different types of myocardial injuries. The patient's thermogram is compared to the reference thermograms. The comparing may use metrics of thermogram features, which are also referred to as distinguishing features. Optionally, the classifier will produce a score representing the probability that the curve is from a patient with thrombotic MI, non-thrombotic myocardial injury or stable CAD.

Details of patients from whom samples may be obtained, processing of whole blood samples to obtain plasma for testing, the dilution and other preparation of plasma for testing, carrying out the DSC, interpreting the thermograms, and analyzing data may be found in patent application publications, including PCT publication numbers WO 2008/089072, WO 2010/033606 and WO 2011/156658, as well as U.S. Pub. No. 2018/0277250, the relevant content of which are hereby incorporated by reference.

If a patient is identified as having a type 1 infarction they may be treated with anti-platelet, anti-coagulant, fibrinolytic or an invasive surgical procedure to clear the thrombus and restore blood flow to the heart muscle. Additional details of consensus recommended treatments for thrombotic (type 1) MI, may be found in practice guidelines published jointly by the American College of Cardiology and the American Heart Association such as: Levine, G. N. et al., "2015 ACC/AHA/SCAI Focused Update on Primary Percutaneous Coronary Intervention for Patients With ST-Elevation Myocardial Infarction: An Update of the 2011 ACCF/AHA/SCAI Guideline for Percutaneous Coronary Intervention and the 2013 ACCF/AHA Guideline for the Management of ST-Elevation Myocardial Infarction", Circulation, Vol. 133, No. 11, pp. 1135-1147 (2016); Amsterdam, E. A., et al., "2014 AHA/ACC Guideline for the Management of Patients With Non-ST-Elevation Acute Coronary Syndromes", Circulation, Vol. 130, No. 25, pp. e344-e426 (2014); and O'Gara, P. T., et al. "2013 ACCF/AHA Guideline for the Management of ST-Elevation Myocardial Infarction" Circulation, Vol. 127, No. 4, pp. e362-e425 (2013), which are incorporated herein by reference (50-52).

EXAMPLES

Example 1

Sample Preparation and Data Preprocessing

Parameters for the collection of DSC data are as follows: temperature range 20-110° C., scan rate of 1° C./min, pre-scan thermostat of 900 seconds. Raw DSC data are then processed as follows: (1) correction of the instrumental baseline by subtraction of a buffer reference scan; (2) normalization for total protein concentration; (3) correction for non-zero sample baselines by application of a linear baseline function. The output of a DSC experiment is the excess heat capacity (sample chamber minus reference chamber) as a function of temperature. Step (1) subtracts the instrument response in the absence of sample (buffer loaded in both instrument chambers) from that in the presence of the sample (sample loaded in the sample chamber and buffer in the reference chamber) to determine the specific heat capacity signal associated with the plasma sample. Subtraction of a buffer reference scan recorded close in time to the sample scan accounts for any slight variation in instrument conditions resulting from baseline drift or changes in ambient conditions, as well as any small differences in the fabrication and temperature characteristics between the two instrument chambers. Step (2) involves normalization of DSC data for the specific protein content of a given sample. Heat capacity is an extensive property, that is, it is proportional to the mass of the substance, thus, normalizing for total protein content allows the direct comparison of plasma samples with different total protein concentrations. Step (3) involves correction of the sample baseline prior to area integration or fitting of the unfolding transition. During the transition the sample comprises a mixture of folded and unfolded forms of all components, each with different heat capacities. The baseline must be selected to estimate the heat capacity of the sample at any temperature during the thermal transition.

As part of the development of DSC as a diagnostic, the effects of specimen handling were tested (time of storage, freeze-thaw cycles, length of storage, sample type); sample preparation (buffer exchange method, filtration method, sample dilution); data collection and processing (scan rate, reproducibility of repeated scans) (53). We tested both healthy control and disease plasmas and showed that thermograms are robust to all tested pre-analytical and analytical variables, except storage at 4° C. for more than two weeks. This provides flexibility in the method of specimen preparation for DSC analysis. Our current preparation procedure involves buffer exchange via dialysis, followed by filtration and 25-fold sample dilution. Other methods were examined for buffer exchange method (dialysis; spin columns; no buffer exchange), filtration method (filtration; no filtration) and sample dilution (100-fold; 50-fold; 25-fold; 10-fold) and give equivalent results. Additionally, there are many approaches available for preprocessing of the raw DSC data. Our current data preprocessing procedure employs normalizing using the total protein concentration followed by a linear sample baseline correction, where the pre-transition region (fully folded components) and the post-transition region (fully unfolded components) are connected by a linear estimated sample baseline. Other methods are available for data normalization (normalization using total protein; normalization using the height of a selected peak in the thermogram) (38, 46) and sample baseline correction (54) (linear baseline; cubic baseline; progress (sigmoidal) baseline; step baseline; spline interpolation).

Example 2

A total of 312 participants were enrolled, resulting in a total of 83 thrombotic MI, 36 acute non-thrombotic myocardial injury, and 53 stable CAD subjects meeting our stringent cohort criteria (Table 1). "Borderline" cases that do not meet the criteria for thrombotic MI, acute non-thrombotic myocardial injury, or stable CAD are eliminated from this phase of the study to limit misclassification. This is by design, as it is most useful to first identify phenotype associated temporal changes given minimal phenotypic confusion or misclassification.

To minimize selection bias, all consecutive-enrolled subjects were enrolled in the cohort to reflect the population distribution of our area. Baseline blood was collected at the time of presentation for cardiac catheterization (prior to any percutaneous coronary intervention) and 2, 4, 24 and 48 hours after enrollment (time of cardiac catheterization). Quiescent state data were obtained when subjects were clinically stable, 3-12 months after enrollment. Detailed medical history, physical assessment, and cardiac catheterization has been recorded. Electrocardiograms were systematically evaluated using established criteria (55-58). Laboratory characterization includes troponin I, D-Dimer and C-reactive protein at all time points. All coronary aspiration attempts were at the discretion of the treating physician and were strained, immediately preserved in formalin, and underwent blinded histological evaluation by an expert pathologist trained in the analysis of coronary thrombosis at CVPath Institute, Inc., Gaithersburg, Maryland (59, 60). Angiograms were examined in a blinded fashion by the Johns Hopkins Quantitative Angiographic Core Laboratory using jointly developed criteria for all study participants (61-67).

TABLE 1

Study criteria for phenotype classification

| Study Phenotype | Requirements |
| --- | --- |
| Thrombotic MI | Histopathological evidence of thrombus 0-3 days old -&- elevated and increasing Troponin I |
| Acute non-thrombotic myocardial injury | No thrombus by histopathology or blinded angiogram assessment, no coronary stenosis >50%, normal TIMI flow and normal TIMI MPG by blinded angiogram assessment, elevated and increasing Troponin I |
| Stable CAD | Elective presentation. No thrombus by histopathology or blinded angiogram assessment, history of prior ASCVD event or ≥50% coronary stenosis noted on angiogram, normal TIMI MPG, troponin I <$99^{th}$ percentile |

ASCVD = atherosclerotic cardiovascular disease;
CAD = coronary artery disease;
MI = myocardial infarction;
TIMI = Thrombolysis in myocardial infarction;
MPG = myocardial perfusion grade

REFERENCES

1. Benjamin E J, Virani S S, Callaway C W, Chamberlain A M, Chang A R, Cheng S, Chiuve S E, Cushman M, Delling F N, Deo R, de Ferranti S D, Ferguson J F, Fornage M, Gillespie C, Isasi C R, Jiménez M C, Jordan L C, Judd S E, Lackland D, Lichtman J H, Lisabeth L, Liu S, Longenecker C T, Lutsey P L, Mackey J S, Matchar D B, Matsushita K, Mussolino M E, Nasir K, O'Flaherty M, Palaniappan L P, Pandey A, Pandey D K, Reeves M J, Ritchey M D, Rodriguez C J, Roth G A, Rosamond W D, Sampson U K A, Satou G M, Shah S H, Spartano N L, Tirschwell D L, Tsao C W, Voeks J H, Willey J Z, Wilkins J T, Wu J H, Alger H M, Wong S S and Muntner P. Heart Disease and Stroke Statistics-2018 Update: A Report From the American Heart Association. Circulation. 2018; 137: e67-e492.
2. DeFilippis A P, Chapman A R, Mills N L, de Lemos J A, Arbab-Zadeh A, Newby L K and Morrow D A. Assessment and Treatment of Patients with Type 2 Myocardial Infarction and Acute Non-Ischemic Myocardial Injury. Circulation. 2019; 140:1661-1678.
3. Newby L K, Jesse R L, Babb J D, Christenson R H, De Fer T M, Diamond G A, Fesmire F M, Geraci S A, Gersh B J, Larsen G C, Kaul S, McKay C R, Philippides G J and Weintraub W S. ACCF 2012 expert consensus document on practical clinical considerations in the interpretation of troponin elevations: a report of the American College of Cardiology Foundation task force on Clinical Expert Consensus Documents. Journal of the American College of Cardiology. 2012; 60:2427-63.
4. Thygesen K, Alpert J S, Jaffe A S, Chaitman B R, Bax J J, Morrow D A and White H D. Fourth Universal Definition of Myocardial Infarction (2018). Circulation. 2018; 138: e618-e651.
5. Amsterdam E A, Wenger N K, Brindis R G, Casey D E, Jr., Ganiats T G, Holmes D R, Jr., Jaffe A S, Jneid H, Kelly R F, Kontos M C, Levine G N, Liebson P R, Mukherjee D, Peterson E D, Sabatine M S, Smalling R W and Zieman S J. 2014 AHA/ACC guideline for the management of patients with non-ST-elevation acute coronary syndromes: executive summary: a report of the American College of Cardiology/American Heart Association Task Force on Practice Guidelines. Circulation. 2014; 130: 2354-94.
6. Collet J P, Thiele H, Barbato E, Barthélémy O, Bauersachs J, Bhatt D L, Dendale P, Dorobantu M, Edvardsen T, Folliguet T, Gale C P, Gilard M, Jobs A, Jüni P, Lambrinou E, Lewis B S, Mehilli J, Meliga E, Merkely B, Mueller C, Roffi M, Rutten F H, Sibbing D and Siontis G C M. 2020 ESC Guidelines for the management of acute coronary syndromes in patients presenting without persistent ST-segment elevation. European heart journal. 2020.
7. O'Gara P T, Kushner F G, Ascheim D D, Casey D E, Jr., Chung M K, de Lemos J A, Ettinger S M, Fang J C, Fesmire F M, Franklin B A, Granger C B, Krumholz H M, Linderbaum J A, Morrow D A, Newby L K, Ornato J P, Ou N, Radford M J, Tamis-Holland J E, Tommaso J E, Tracy C M, Woo Y J and Zhao D X. 2013 ACCF/AHA guideline for the management of ST-elevation myocardial infarction: executive summary: a report of the American College of Cardiology Foundation/American Heart Association Task Force on Practice Guidelines. Circulation. 2013; 127:529-55.
8. Tamis-Holland J E, Jneid H, Reynolds H R, Agewall S, Brilakis E S, Brown T M, Lerman A, Cushman M, Kumbhani D J, Arslanian-Engoren C, Bolger A F and Beltrame J F. Contemporary Diagnosis and Management of Patients With Myocardial Infarction in the Absence of Obstructive Coronary Artery Disease: A Scientific Statement From the American Heart Association. Circulation. 2019; 139: e891-e908.
9. Sarkisian L, Saaby L, Poulsen T S, Gerke O, Hosbond S, Jangaard N, Diederichsen A C, Thygesen K and Mickley H. Prognostic Impact of Myocardial Injury Related to Various Cardiac and Noncardiac Conditions. The American journal of medicine. 2016; 129:506-514 e1.
10. Gore M O, Seliger S L, Defilippi C R, Nambi V, Christenson R H, Hashim I A, Hoogeveen R C, Ayers C R, Sun W, McGuire D K, Ballantyne C M and de Lemos J A. Age- and sex-dependent upper reference limits for the high-sensitivity cardiac troponin T assay. Journal of the American College of Cardiology. 2014; 63:1441-8.
11. Javed U, Aftab W, Ambrose J A, Wessel R J, Mouanoutoua M, Huang G, Barua R S, Weilert M, Sy F and Thatai D. Frequency of elevated troponin I and diagnosis of acute myocardial infarction. The American journal of cardiology. 2009; 104:9-13.
12. Wong P, Murray S, Ramsewak A, Robinson A, van Heyningen C and Rodrigues E. Raised cardiac troponin T levels in patients without acute coronary syndrome. Postgraduate medical journal. 2007; 83:200-5.
13. Wong P, Ramsewak A, Murray S, Robinson A, Robinson D and Rodrigues E. Effects of comorbidity and hospital care on 6-month mortality in patients with elevated cardiac troponin T. Postgraduate medical journal. 2007; 83:332-7.

14. Wong P S, Jones J D, Ashrafi R, Khanzada O, Wickramarachchi U, Keen T H and Robinson D R. Early and late mortality in hospitalised patients with raised cardiac troponin T. Postgraduate medical journal. 2012; 88:437-42.
15. Pitts S R, Niska R W, Xu J and Burt C W. National Hospital Ambulatory Medical Care Survey: 2006 emergency department summary. National health statistics reports. 2008:1-38.
16. Pope J H, Aufderheide T P, Ruthazer R, Woolard R H, Feldman J A, Beshansky J R, Griffith J L and Selker H P. Missed diagnoses of acute cardiac ischemia in the emergency department. The New England journal of medicine. 2000; 342:1163-70.
17. Tatum J L, Jesse R L, Kontos M C, Nicholson C S, Schmidt K L, Roberts C S and Ornato J P. Comprehensive strategy for the evaluation and triage of the chest pain patient. Annals of emergency medicine. 1997; 29:116-25.
18. Jneid H, Addison D, Bhatt D L, Fonarow G C, Gokak S, Grady K L, Green L A, Heidenreich P A, Ho P M, Jurgens C Y, King M L, Kumbhani D J and Pancholy S. 2017 AHA/ACC Clinical Performance and Quality Measures for Adults With ST-Elevation and Non-ST-Elevation Myocardial Infarction: A Report of the American College of Cardiology/American Heart Association Task Force on Performance Measures. Journal of the American College of Cardiology. 2017; 70:2048-2090.
19. Antman E. Fibrinolytic therapy. In: Braunwald's Heart disease: A textbook of cardiovascular medicine. 7th ed. Philadelphia: Saunders; 2005.
20. Bueno H, Martinez-Selles M, Perez-David E and Lopez-Palop R. Effect of thrombolytic therapy on the risk of cardiac rupture and mortality in older patients with first acute myocardial infarction. European heart journal. 2005; 26:1705-11.
21. Wallentin L, Goldstein P, Armstrong P W, Granger C B, Adgey A A, Arntz H R, Bogaerts K, Danays T, Lindahl B, Makijarvi M, Verheugt F and Van de Werf F. Efficacy and safety of tenecteplase in combination with the low-molecular-weight heparin enoxaparin or unfractionated heparin in the prehospital setting: the Assessment of the Safety and Efficacy of a New Thrombolytic Regimen (ASSENT)-3 PLUS randomized trial in acute myocardial infarction. Circulation. 2003; 108:135-42.
22. Mehta L S. Acute Myocardial Infarction in Women A Scientific Statement From the American Heart Association. Circulation. 2016; 133:916-947.
23. Culic V, Eterovic D, Miric D and Silic N. Symptom presentation of acute myocardial infarction: Influence of sex, age, and risk factors. Am Heart J. 2002; 144:1012-1017.
24. DeFilippis A P, Nasir K, Blaha M J. Myocardial Infarction as a Clinical End Point in Research. Circ Res. 2019 Jun. 7; 124(12):1701-1703.
25. DeFilippis A P, Trainor P J, Hill B G, Amraotkar A R, Rai S N, Hirsch G A, Rouchka E C and Bhatnagar A. Identification of a plasma metabolomic signature of thrombotic myocardial infarction that is distinct from non-thrombotic myocardial infarction and stable coronary artery disease. PloS one. 2017; 12: e0175591.
26. Trainor P J, Hill B G, Carlisle S M, Rouchka E C, Rai S N, Bhatnagar A and DeFilippis A P. Systems characterization of differential plasma metabolome perturbations following thrombotic and non-thrombotic myocardial infarction. Journal of proteomics. 2017; 160:38-46.
27. Trainor P J, Yampolskiy R V and DeFilippis A P. Wisdom of artificial crowds feature selection in untargeted metabolomics: An application to the development of a blood-based diagnostic test for thrombotic myocardial infarction. Journal of biomedical informatics. 2018; 81:53-60.
28. Trainor P J, DeFilippis A P and Rai S N. Evaluation of Classifier Performance for Multiclass Phenotype Discrimination in Untargeted Metabolomics. Metabolites. 2017; 7.
29. Garbett N C, Mekmaysy C S, Helm C W, Jenson A B and Chaires J B.
Differential scanning calorimetry of blood plasma for clinical diagnosis and monitoring. Experimental and molecular pathology. 2009; 86:186-91.
30. Garbett N C, Miller J J, Jenson A B and Chaires J B. Calorimetry outside the box: a new window into the plasma proteome. Biophysical journal. 2008; 94:1377-83.
31. Garbett N C, Miller J J, Jenson A B and Chaires J B. Calorimetric analysis of the plasma proteome. Seminars in nephrology. 2007; 27:621-6.
32. Garbett N C, Miller J J, Jenson A B, Miller D M and Chaires J B. Interrogation of the plasma proteome with differential scanning calorimetry. Clinical chemistry. 2007; 53:2012-4.
33. Garbett N C, Miller J J, Jenson A B and Chaires J B. Ligand Binding Alters the Calorimetric Thermogram of Albumin. J Clin Ligand Assay. 2006; 29:194-197.
34. Garbett N C, Merchant M L, Chaires J B and Klein J B. Calorimetric analysis of the plasma proteome: identification of type 1 diabetes patients with early renal function decline. Biochimica et biophysica acta. 2013; 1830:4675-80.
35. Garbett N C, Merchant M L, Helm C W, Jenson A B, Klein J B and Chaires J B. Detection of cervical cancer biomarker patterns in blood plasma and urine by differential scanning calorimetry and mass spectrometry. PloS one. 2014; 9: e84710.
36. Garbett N C, Brock G N, Chaires J B, Mekmaysy C S, DeLeeuw L, Sivils K L, Harley J B, Rovin B H, Kulasekera K B and Jarjour W N. Characterization and classification of lupus patients based on plasma thermograms. PloS one. 2017; 12: e0186398.
37. Kendrick S K, Zheng Q, Garbett N C and Brock G N. Application and interpretation of functional data analysis techniques to differential scanning calorimetry data from lupus patients. PloS one. 2017; 12: e0186232.
38. Velazquez-Campoy A, Vega S, Sanchez-Gracia O, Lanas A, Rodrigo A, Kaliappan A, Hall M B, Nguyen T Q, Brock G N, Chesney J A, Garbett N C and Abian O. Thermal liquid biopsy for monitoring melanoma patients under surveillance during treatment: A pilot study. Biochimica et biophysica acta General subjects. 2018; 1862:1701-1710.
39. Fekecs T, Zapf I, Ferencz A and Lőrinczy D. Differential scanning calorimetry (DSC) analysis of human plasma in melanoma patients with or without regional lymph node metastases. J Therm Anal Calorim. 2012; 108:149-152.
40. Michnik A, Drzazga Z, Michalik K, Barczyk A, Santura I, Sozańska E and Pierzchała W. Differential scanning calorimetry study of blood serum in chronic obstructive pulmonary disease. J Therm Anal Calorim. 2010; 102:57-60.
41. Todinova S, Krumova S, Gartcheva L, Robeerst C and Taneva S G. Microcalorimetry of blood serum proteome: a modified interaction network in the multiple myeloma case. Analytical chemistry. 2011; 83:7992-8.
42. Todinova S, Krumova S, Kurtev P, Dimitrov V, Djongov L, Dudunkov Z and Taneva S G. Calorimetry-based profiling of blood plasma from colorectal cancer patients. Biochimica et biophysica acta. 2012; 1820:1879-85.
43. Zapf I, Fekecs T, Ferencz A, Tizedes G, Pavlovics G, Kálmán E and Lőrinczy D. DSC analysis of human plasma in breast cancer patients. Thermochim Acta. 2011; 524:88-91.
44. Chagovetz A A, Jensen R L, Recht L, Glantz M and Chagovetz A M.
Preliminary use of differential scanning calorimetry of cerebrospinal fluid for the diagnosis of glioblastoma multiforme. Journal of neuro-oncology. 2011; 105:499-506.
45. Chagovetz A A, Quinn C, Damarse N, Hansen L D, Chagovetz A M and Jensen R L. Differential scanning calorimetry of gliomas: a new tool in brain cancer diagnostics? Neurosurgery. 2013; 73:289-95; discussion 295.
46. Vega S, Garcia-Gonzalez M A, Lanas A, Velazquez-Campoy A and Abian O. Deconvolution analysis for classifying gastric adenocarcinoma patients based on differential scanning calorimetry serum thermograms. Scientific reports. 2015; 5:7988.
47. Krumova S, Todinova S, Mavrov D, Marinov P, Atanassova V, Atanassov K and Taneva S G. Intercriteria analysis of calorimetric data of blood serum proteome. Biochimica et biophysica acta General subjects. 2017; 1861:409-417.
48. Todinova S, Krumova S, Danailova A, Petkova V, Guenova M, Mihaylov G, Gartcheva L and Taneva S G. Calorimetric markers for monitoring of multiple myeloma and Waldenstrom's macroglobulinemia patients. European biophysics journal: EBJ. 2018; 47:549-559.
49. Todinova S, Krumova S, Radoeva R, Gartcheva L and Taneva S G. Calorimetric markers of Bence Jones and nonsecretory multiple myeloma serum proteome. Analytical chemistry. 2014; 86:12355-61.
50. Levine, G. N. et al., "2015 ACC/AHA/SCAI Focused Update on Primary Percutaneous Coronary Intervention for Patients With ST-Elevation Myocardial Infarction: An Update of the 2011 ACCF/AHA/SCAI Guideline for Percutaneous Coronary Intervention and the 2013 ACCF/AHA Guideline for the Management of ST-Elevation Myocardial Infarction", Circulation, Vol. 133, No. 11, pp. 1135-1147 (2016).
51. Amsterdam, E. A., et al., "2014 AHA/ACC Guideline for the Management of Patients With Non-ST-Elevation Acute Coronary Syndromes", Circulation, Vol. 130, No. 25, pp. e344-e426 (2014).
52. O'Gara, P. T., et al. "2013 ACCF/AHA Guideline for the Management of ST-Elevation Myocardial Infarction" Circulation, Vol. 127, No. 4, pp. e362-e425 (2013).
53. Garbett N C, Mekmaysy C S, DeLeeuw L and Chaires J B. Clinical application of plasma thermograms. Utility, practical approaches and considerations. Methods. 2015; 76:41-50.
54. Cooper A, Nutley M and Wadood A. Differential scanning microcalorimetry. In: B. Chowdhry and S. Harding, eds. Protein-Ligand Interactions: hydrodynamics and calorimetry: a practical approach Oxford, UK: Oxford University Press; 2001: 287-318.
55. Kramer M C, Rittersma S Z, de Winter R J, Ladich E R, Fowler D R, Liang Y H, Kutys R, Carter-Monroe N, Kolodgie F D, van der Wal A C and Virmani R. Relationship of thrombus healing to underlying plaque morphology in sudden coronary death. Journal of the American College of Cardiology. 2010; 55:122-32.
56. Kramer M C, van der Wal A C, Koch K T, Ploegmakers J P, van der Schaaf R J, Henriques J P, Baan J, Jr., Rittersma S Z, Vis M M, Piek J J, Tijssen J G and de Winter R J. Presence of older thrombus is an independent predictor of long-term mortality in patients with ST-elevation myocardial infarction treated with thrombus aspiration during primary percutaneous coronary intervention. Circulation. 2008; 118:1810-6.
57. Thygesen K, Alpert J S, Jaffe A S, Simoons M L, Chaitman B R, White H D, Writing Group on behalf of the Joint ESC ACCF AHA WHF Task Force for the Universal Definition of Myocardial Infarction, Katus H A, Lindahl B, Morrow D A, Clemmensen P M, Johanson P, Hod H, Underwood R, Bax J J, Bonow R O, Pinto F, Gibbons R J, Fox K A, Atar D, Newby L K, Galvani M, Hamm C W, Uretsky B F, Steg P G, Wijns W, Bassand J P, Menasche P, Ravkilde J, Ohman E M, Antman E M, Wallentin L C, Armstrong P W, Simoons M L, Januzzi J L, Nieminen M S, Gheorghiade M, Filippatos G, Luepker R V, Fortmann S P, Rosamond W D, Levy D, Wood D, Smith S C, Hu D, Lopez-Sendon J L, Robertson R M, Weaver D, Tendera M, Bove A A, Parkhomenko A N, Vasilieva E J and Mendis S. Third universal definition of myocardial infarction. Circulation. 2012; 126:2020-35.
58. Wagner G S, Macfarlane P, Wellens H, Josephson M, Gorgels A, Mirvis D M, Pahlm O, Surawicz B, Kligfield P, Childers R, Gettes L S, Bailey J J, Deal B J, Gorgels A, Hancock E W, Kors J A, Mason J W, Okin P, Rautaharju P M, van Herpen G, American Heart Association E, Arrhythmias Committee CoCC, American College of Cardiology F and Heart Rhythm S. AHA/ACCF/HRS recommendations for the standardization and interpretation of the electrocardiogram: part VI: acute ischemia/infarction: a scientific statement from the American Heart Association Electrocardiography and Arrhythmias Committee, Council on Clinical Cardiology; the American College of Cardiology Foundation; and the Heart Rhythm Society. Endorsed by the International Society for Computerized Electrocardiology. Journal of the American College of Cardiology. 2009; 53:1003-11.
59. Ambrose J A, Almeida O D, Sharma S K, Dangas G and Ratner D E. Angiographic evolution of intracoronary thrombus and dissection following percutaneous transluminal coronary angioplasty (the Thrombolysis and Angioplasty in Unstable Angina [TAUSA] trial). The American journal of cardiology. 1997; 79:559-63.
60. Ambrose J A, Almeida O D, Sharma S K, Torre S R, Marmur J D, Israel D H, Ratner D E, Weiss M B, Hjemdahl-Monsen C E, Myler R K and et al. Adjunctive thrombolytic therapy during angioplasty for ischemic rest angina. Results of the TAUSA Trial. TAUSA Investigators. Thrombolysis and Angioplasty in Unstable Angina trial. Circulation. 1994; 90:69-77.
61. Ambrose J A and Israel D H. Angiography in unstable angina. The American journal of cardiology. 1991; 68:78B-84B.
62. Capone G, Wolf N M, Meyer B and Meister S G. Frequency of intracoronary filling defects by angiography in angina pectoris at rest. The American journal of cardiology. 1985; 56:403-6.
63. Dangas G, Mehran R, Wallenstein S, Courcoutsakis N A, Kakarala V, Hollywood J and Ambrose J A. Correlation of angiographic morphology and clinical presentation in unstable angina. Journal of the American College of Cardiology. 1997; 29:519-25.
64. Gibson C M, Cannon C P, Murphy S A, Marble S J, Barron H V, Braunwald E and Group TS. Relationship of the TIMI myocardial perfusion grades, flow grades, frame count, and percutaneous coronary intervention to long-term outcomes after thrombolytic administration in acute myocardial infarction. Circulation. 2002; 105:1909-13.
65. Gibson C M, Cannon C P, Murphy S A, Ryan K A, Mesley R, Marble S J, McCabe C H, Van De Werf F and Braunwald E. Relationship of TIMI myocardial perfusion grade to mortality after administration of thrombolytic drugs. Circulation. 2000; 101:125-30.
66. Goldstein J A, Demetriou D, Grines C L, Pica M, Shoukfeh M and O'Neill W W. Multiple complex coronary plaques in patients with acute myocardial infarction. The New England journal of medicine. 2000; 343:915-22.
67. Zack P M, lschinger T, Aker U T, Dincer B and Kennedy H L. The occurrence of angiographically detected intracoronary thrombus in patients with unstable angina pectoris. Am Heart J. 1984; 108:1408-12.

What is claimed is:

1. A method of diagnosing and treating a patient showing symptoms of acute myocardial infarction, comprising:
   obtaining a plasma sample from the patient,
   performing a differential scanning calorimetry test on the sample to produce a thermogram,
   comparing the thermogram to reference thermograms,
   determining that the patient has thrombotic myocardial infarction, and
   administering a treatment to the patient based on the thermogram,
   wherein the treatment comprises at least one member selected from the group consisting of anti-platelet therapies, anti-coagulant therapies, fibrinolytic therapies and procedural revascularization therapies.

2. The method of claim 1, wherein the treatment comprises anti-platelet therapies.

3. The method of claim 1, wherein the treatment comprises anti-coagulant therapies.

4. The method of claim 1, wherein the treatment comprises fibrinolytic therapies.

5. The method of claim 1, wherein the treatment comprises procedural revascularization therapies.

6. The method of claim 1, wherein obtaining a plasma sample from the patient comprises:
   isolating the plasma from whole blood, and
   diluting the sample.

7. The method of claim 1, wherein comparing the thermogram to reference thermograms comprises comparing distinguishing features, and
   the distinguishing features are selected from the group consisting of (1) thermogram peak width at half height (width); (2) maximum profile height (height); (3) temperature of the profile maximum ($T_{max}$); (4) first moment temperature ($T_{FM}$) representing the weighted center of the profile; (5) excess specific heat capacity ($C_p^{ex}$) of the first thermogram peak in the range 62-67° C. ($C_p^{ex}$ Peak 1); (6) excess specific heat capacity of the second thermogram peak in the range 69-73° C. ($C_p^{ex}$ Peak 2); (7) ratio of $C_p^{ex}$ Peak 1 to $C_p^{ex}$ Peak 2; and (8) principal components, or combinations thereof.

8. The method of claim 1, wherein comparing the thermogram to the reference thermograms comprises comparing the thermogram and the reference thermograms by visual inspection.

9. The method of claim 1, further comprising generating a probability score for thrombotic myocardial infarction.

10. The method of claim 1, wherein the patient has received a positive troponin test.

* * * * *